(12) United States Patent
Hareyama et al.

(10) Patent No.: US 6,764,485 B2
(45) Date of Patent: Jul. 20, 2004

(54) THERMAL TREATMENT APPARATUS

(75) Inventors: Norihiko Hareyama, Tokyo (JP); Takefumi Uesugi, Tokyo (JP); Taisuke Sato, Tokyo (JP); Shigenobu Iwahashi, Kanagawa (JP); Shigeki Ariura, Kanagawa (JP); Wataru Karino, Kanagawa (JP); Makoto Inaba, Tokyo (JP); Shin Maki, Kanagawa (JP)

(73) Assignees: Olympus Optical Co., Ltd., Tokyo (JP); Terumo Kabushiki Kaisha, Tokyo (JP)

( * ) Notice: Subject to any disclaimer, the term of this patent is extended or adjusted under 35 U.S.C. 154(b) by 203 days.

(21) Appl. No.: 10/180,489

(22) Filed: Jun. 27, 2002

(65) Prior Publication Data

US 2003/0065315 A1 Apr. 3, 2003

(30) Foreign Application Priority Data

Jun. 29, 2001 (JP) ........................................ 2001-198786

(51) Int. Cl.$^7$ ............................................... A61B 18/20
(52) U.S. Cl. ............................. 606/11; 606/13; 606/18
(58) Field of Search ............................... 606/2, 11, 15, 606/17, 18, 19

(56) References Cited

U.S. PATENT DOCUMENTS

| 4,932,956 | A | | 6/1990 | Reddy et al. | |
| 5,207,672 | A | | 5/1993 | Roth et al. | |
| 5,292,320 | A | | 3/1994 | Brown et al. | |
| 5,496,308 | A | | 3/1996 | Brown et al. | |
| 5,788,688 | A | * | 8/1998 | Bauer et al. | 606/1 |
| 6,379,347 | B1 | * | 4/2002 | Maki et al. | 606/17 |
| 6,544,257 | B2 | * | 4/2003 | Nagase et al. | 606/15 |
| 6,562,029 | B2 | * | 5/2003 | Maki et al. | 606/17 |
| 6,599,287 | B2 | * | 7/2003 | Iwahashi et al. | 606/14 |
| 6,605,082 | B2 | * | 8/2003 | Hareyama et al. | 606/11 |

FOREIGN PATENT DOCUMENTS

| EP | 0 673 627 | 9/1995 |
| WO | WO 92/04934 | 4/1992 |
| WO | WO 93/04727 | 3/1993 |

* cited by examiner

Primary Examiner—Michael Peffley
Assistant Examiner—H. M. Johnson
(74) Attorney, Agent, or Firm—Burns, Doane, Swecker & Mathis, L.L.P.

(57) ABSTRACT

The thermal treatment apparatus is equipped with a laser generator for supplying laser beams, a laser irradiation unit for applying the supplied laser beams to tissues, and a control unit for totally controlling various parts of the system. The laser irradiation unit is equipped with a movable laser emission part for emitting laser beams to tissues, a motor for reciprocating a laser emission part, and a guide lumen for supporting an endoscope in such a way as to enable it to move in the direction of the laser emission part. The control unit controls the motor that drives the laser emission part to make reciprocation motion in such a way that the laser emission part stops at a position where it does not interfere with the moving passage of the endoscope.

26 Claims, 31 Drawing Sheets

THERMAL TREATMENT APPARATUS

BACKGROUND OF THE INVENTION

1. Field of the Invention

The invention is related to a thermal treatment apparatus for thermally treating by inserting an insertion unit into a human body either via a body cavity or a lumen such as blood vessels, urethra and abdominal cavity, or pressing its pressing part against a vital tissue surgically or on the body surface, and then irradiating a vital tissue with the energy such as laser beam, microwave, radio frequency, and ultrasound from its emission part provided at the insertion unit or the pressing part.

2. Description of the Related Art

Various thermal treatment apparatuses have been know for treating lesions to reduce or eliminate them by means of heating, degeneration, necrosis, coagulation, cauterization or vaporization of lesions by irradiating them with the energy, such as laser beam, microwave, radio frequency, and ultrasound, with a long and slender insertion unit inserted into a living body either via a body cavity or an opening produced by a small incision.

For example, in applying thermal treatment to benign prostatic hyperplasia, a thermal treatment apparatus is used for treating the prostate transurethrally using laser beams, etc., due to the prostate's position that surrounds the rear part of the urethra. In such a treatment of benign prostatic hyperplasia, a technology has been proposed for concentrating laser beams at the target site located deep inside a tissue by changing the emitting angle of laser beams continuously while reciprocating the laser emission part longitudinally inside the insertion area after the long insertion unit has been inserted into the urethra. This makes it possible to treat only the target area thermally while maintaining areas other than the target area at low temperatures. Moreover, since an endoscope is provided in the insertion unit of the thermal treatment apparatus, the lesion can be visually confirmed prior to the laser beam treatment.

However, in the abovementioned thermal treatment apparatus, the laser emission part is located ahead of the endoscope inside the insertion unit. Therefore, in order to move the endoscope toward the distal part in the insertion unit in order to have a front observation, it used to be necessary to retract the laser emission part manually to the position where it does not interfere with the moving path of the endoscope. Thus, it used to require complex procedures in order to make observations by means of the endoscope. Furthermore, there used to be a danger of damaging the laser emission part or the endoscope, if the endoscope is moved toward the distal side of the insertion unit by mistake, when the laser emission part is not in the retracted position.

Moreover, the laser emission part is driven reciprocatingly, for example, as the rotating motion of a motor provided in the proximal unit of the insertion unit is converted into a linear reciprocating motion. The reciprocating motion of the laser emission part is monitored by means of measuring the motor rpm. However, there has been a problem that, when some damages or separations occur in the connecting mechanism between the motor and the laser emission part, the abnormality cannot be detected even though the abnormality results in a problem of the reciprocating motion of the laser emission part.

On the other hand, the thermal treatment apparatus can be controlled by presetting the irradiation time in addition to the energy power, so that the energy irradiation can be stopped automatically when a preset irradiation time has elapsed since the energy irradiation started, in order to regulate the heat quantity delivered to the tissue.

However, it is necessary for a thermal treatment device to reset the energy irradiation time when the prescribed time has passed and the energy irradiation has stopped.

This makes it very difficult to make a judgment how long irradiation time needs to be added in order to achieve a proper treatment effect as the temperature of the tissue, which has been heated by applying energy, lowers while the irradiation time is being reset.

Moreover, since the thermal treatment requires procedures in a sterilized area, the equipment used repeatedly for setting the energy power and the irradiation time, which is difficult to maintain a sterilized condition, is placed outside of the sterilized area. Therefore, the user who is in a sterilized area cannot reset the irradiation time directly. This means that the user has to ask another person to reset the irradiation time, so that the user cannot reset the irradiation time based on an instant decision and may not be able to perform treatments adequately.

On the other hand, the laser irradiation unit has a shorter life compared to the laser generator and is replaced and discarded after being used only once or several times.

Consequently, the energy transmission efficiency of the thermal apparatus tends to fluctuate each time when the energy irradiation unit is replaced. This caused a problem of instability in the heating performance for the treatment as the energy irradiated on the living body varies with the energy irradiation unit even if the energy generated by the energy supply unit is maintained constant.

In order to solve these problems, an apparatus has been disclosed, for example, by Japanese Patent Laid-Open No. JP-A-57-78845, which measures the energy irradiated by the energy irradiation unit each time a treatment is performed and calibrates the energy generated by the energy supply unit so that the desired energy can be irradiated by the energy irradiation unit.

This apparatus may not be able to perform accurate measurements as the operator has to measure the energy irradiated by the energy irradiation unit. Moreover, even if it is possible make an accurate measurement, it is extremely difficult to measure energy without causing contamination of the energy irradiation unit using an unsterilized measuring device. Under such a circumstance, it used to require very complex procedures such as the necessity of preparation of a port member or a connecting member in order to prevent contaminations.

SUMMARY OF THE INVENTION

It is an object of the present invention to provide a thermal treatment apparatus that is capable of providing a good reciprocating motion of the energy emission part and achieving an excellent treatment effect by properly applying energy to the lesion of the object.

According to an aspect of the invention, there is provided a thermal treatment apparatus comprising: an energy supply unit for supplying energy for treatment; an energy irradiation unit for applying energy supplied by the energy supply unit to a vital tissue, the energy irradiation unit having a movable energy emission part for emitting energy toward the tissue, a driving device for causing the energy emission part to reciprocate, and a guide lumen that supports an observation member for observing the tissue in such a way as to be able to move in the direction of the movement of the energy emission part; and a control unit for controlling the energy emission part to stop at a position where the energy emission part does not interfere with the moving passage of the observing member when stopping the motion of the driving device.

According to another aspect of the invention, there is provided a thermal treatment apparatus comprising: an energy supply unit for supplying energy for treatment; an energy irradiation unit for applying energy supplied by the energy supply unit to a vital tissue, the energy irradiation unit having a movable energy emission part for emitting energy toward the tissue, a driving device for causing the energy emission part to reciprocate, a guide lumen that supports an observation member for observing the tissue in such a way as to be able to move in the direction of the movement of the energy emission part, and a motion detection device for detecting the movement of the observing member to a specified position; and a control unit for controlling the energy emission part to stop when the movement of the observing member to the specified position is detected.

According to still another aspect of the invention, there is provided a thermal treatment apparatus comprising: an energy supply unit for supplying energy for treatment; an energy irradiation unit for applying energy supplied by the energy supply unit to a vital tissue, the energy irradiation unit having a movable energy emission part for emitting energy toward the tissue, a driving device for causing the energy emission part to reciprocate, and a reciprocating motion detection device for detecting the reciprocating motion of the energy emission part; an irradiation operating unit for instructing the energy supply unit to start or stop the supply of energy; and a control unit for controlling the energy emission part to conduct reciprocating motion and for causing the energy supply unit to start supplying energy if the result of detection by the reciprocating motion detection device meets a specified tolerance condition within a specified time period when an energy supply start instruction is received from the irradiation operating unit.

The objects, features, and characterization of this invention other than those set forth above will become apparent from the description given herein below with reference to preferred embodiments illustrated in the accompanying drawings.

DETAILED DESCRIPTIONS OF PREFERRED EMBODIMENTS

Preferred embodiments of the present invention will be described below referring to the accompanying drawings.

Figure 1:
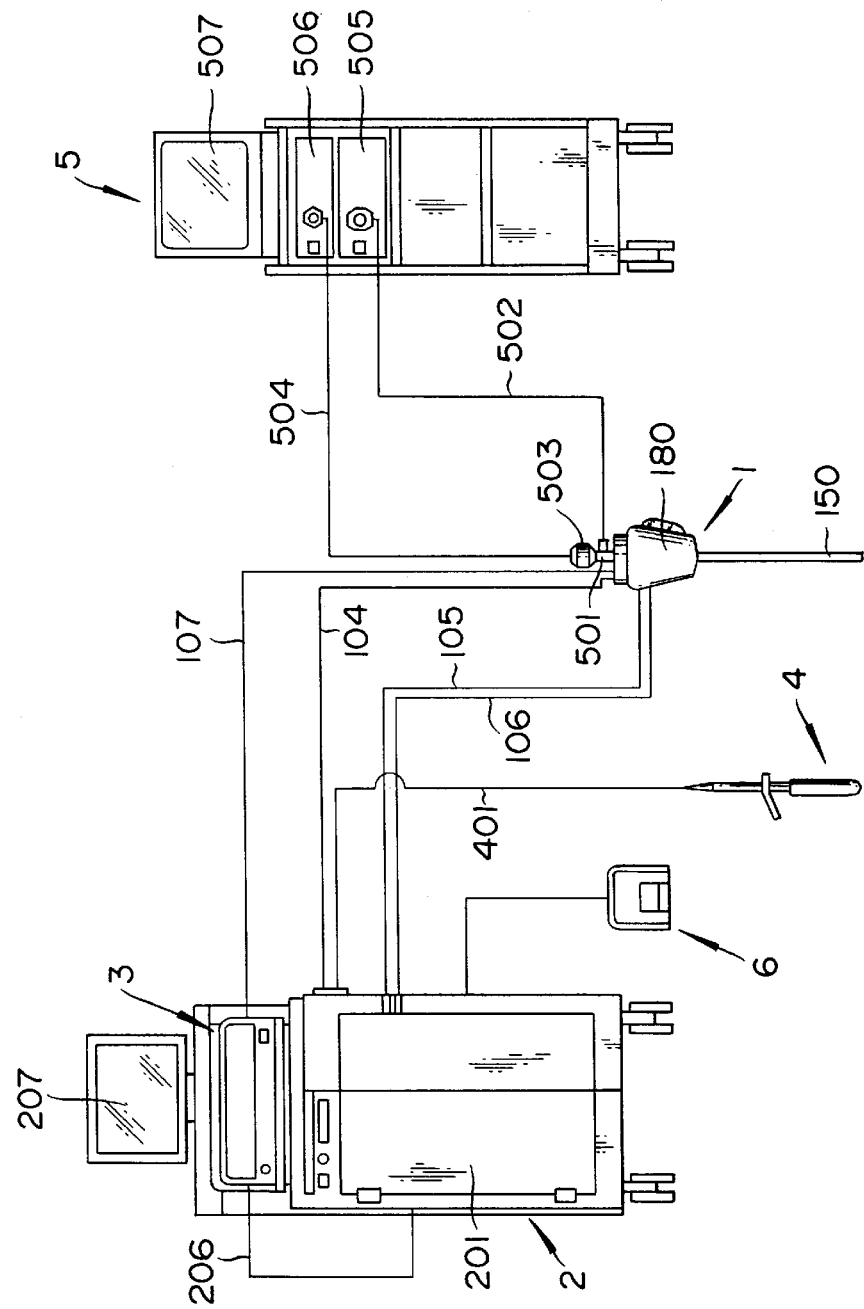
FIG. 1 shows a system constitution of a thermal treatment apparatus according to a first embodiment of the invention.

[Embodiment 1] FIG. 1 shows a system constitution of a thermal treatment apparatus according to a first embodiment of the invention.

The thermal treatment apparatus of the present embodiment includes a laser irradiation unit (urethra probe) 1 as an energy irradiation unit, a main controller 2, a laser generator 3 as an energy supply unit, a rectum probe 4, a foot switch 6 as an irradiation operating unit, and an endoscopes system 5. The laser irradiation unit 1, the laser generator 3, the rectum probe 4, and the foot switch 6 are all connected to the main controller 2. The foot switch 6 outputs a signal to prompt the main controller 2 to start laser beam irradiation when the operator steps it on.

Figure 2:
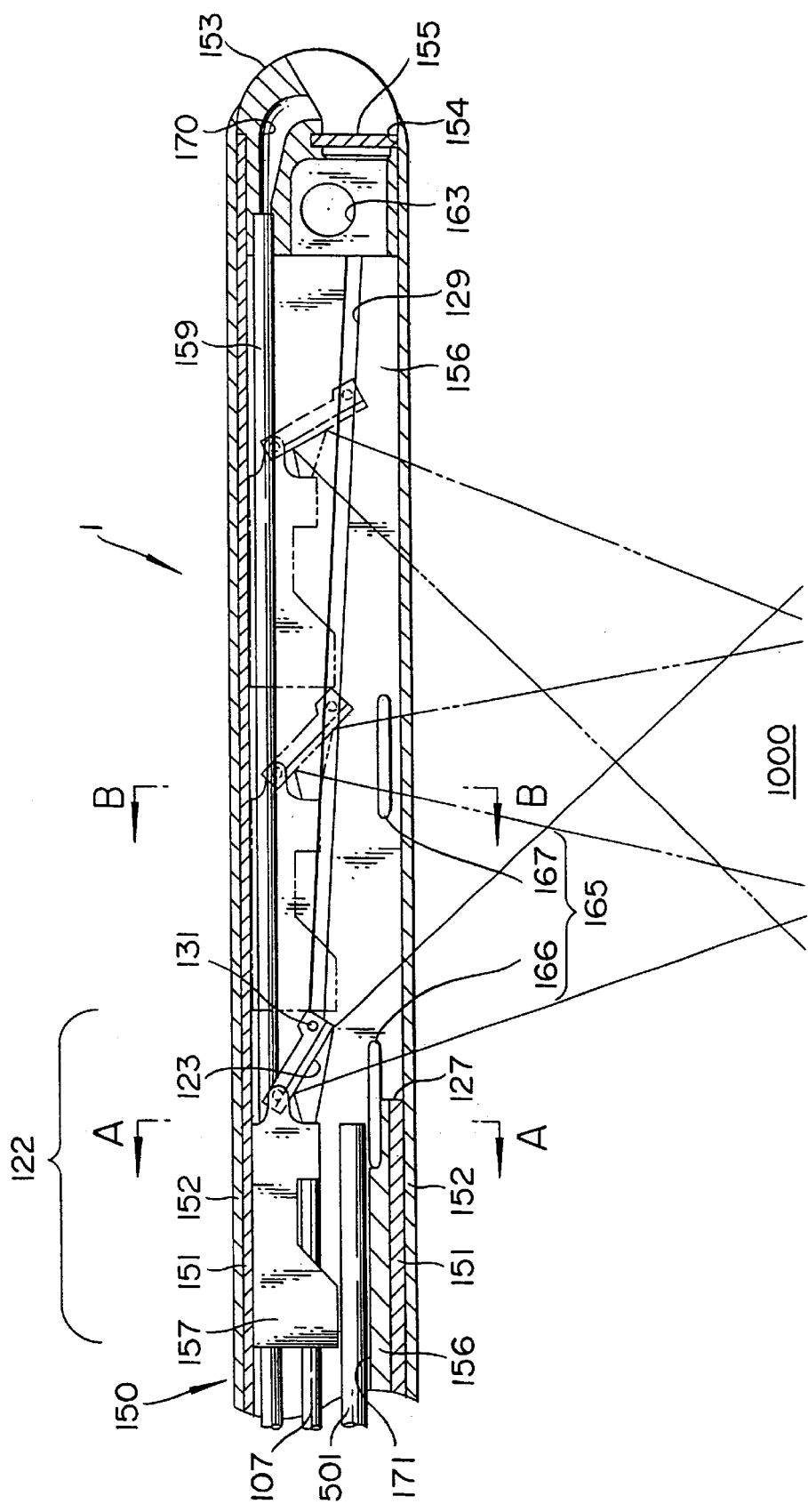
FIG. 2 shows a cross section of the distal part of a laser irradiation unit.
Figure 3:
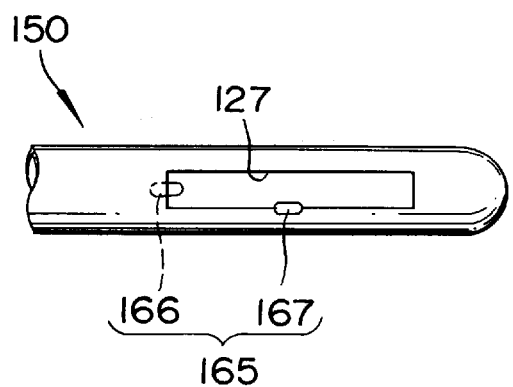
FIG. 3 is a schematic bottom view of FIG. 2.
Figure 4:
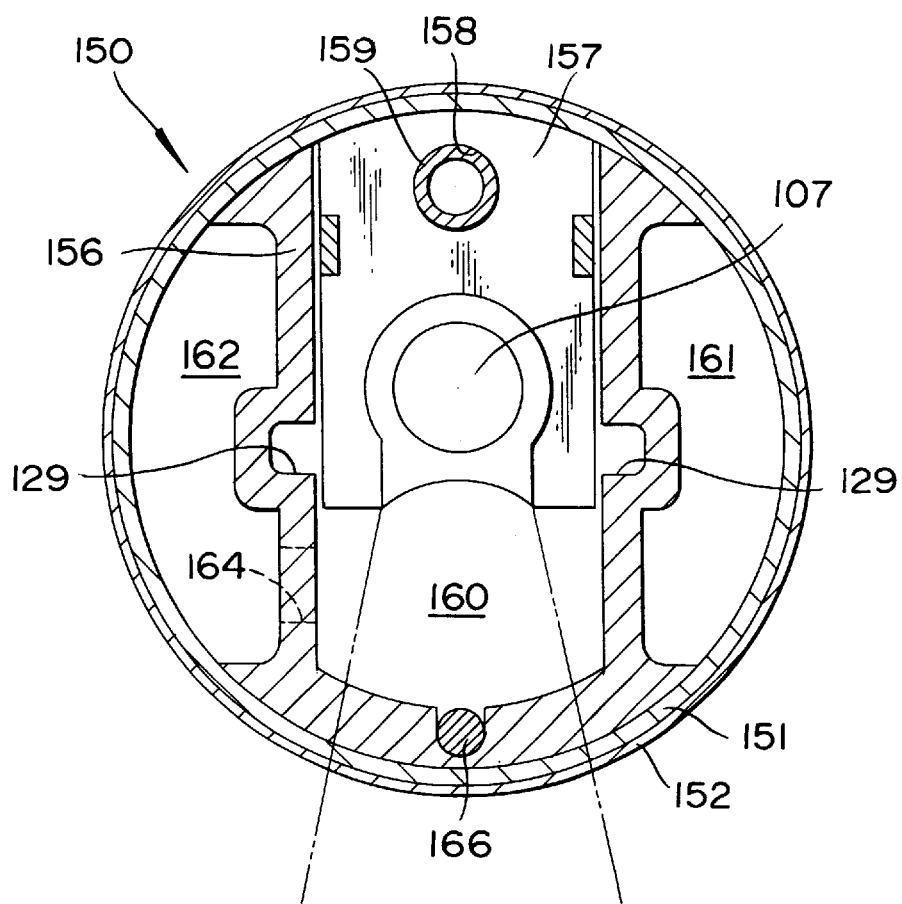
FIG. 4 is a cross sectional view along line A—A of FIG. 2.
Figure 5:
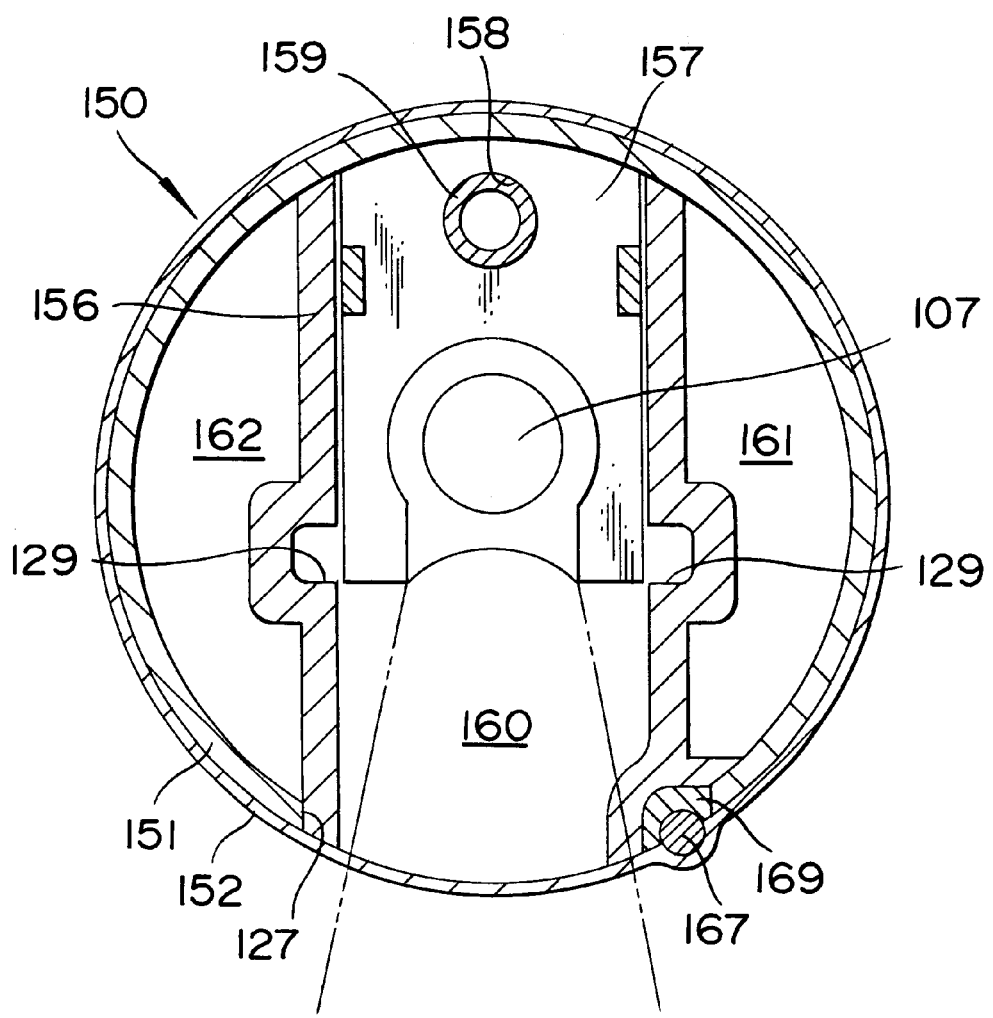
FIG. 5 is a cross sectional view along line B—B of FIG. 2.

FIG. 2 shows a cross section of the distal part of a laser irradiation unit, FIG. 3 is a schematic bottom view of FIG. 2, FIG. 4 is a cross sectional view along line A—A of FIG. 2, and FIG. 5 is a cross sectional view along line B—B of FIG. 2.

The laser irradiation unit 1 of the present embodiment is a laser irradiation unit of a side emitting type that emits laser beams sidewise toward a tissue from its distal part. This thermal treatment apparatus is to perform thermal treatments for benign prostatic hyperplasia or various tumors such as cancers by inserting a long insertion unit 150 of the laser-irradiating apparatus 1 into the urethra, and irradiating tissues with laser beams from a laser emission part 122, which is provided in the insertion unit 150 as the energy emission part. The laser irradiation unit 1 consists of an inserting unit 150 and a proximal unit 180, which is to be gripped by the operator.

As shown in FIG. 2, the insertion unit 150 of the laser irradiation unit 1 has an inner layer pipe 151 comprising the long main body. At the distal part of the insertion unit 150, a laser emission part 122 is provided for emitting or irradiating laser beams. The laser emission part 122 has a tip of the optical fiber 107, a fastening piece 157 affixed to the vicinity of the tip, and a flat laser reflecting-surface (mirror) 123 rotatably attached to the fastening piece 157 for reflecting laser beams.

The inner layer pipe 151 of the insertion unit 150 consists of a hard tube-like member made of stainless steel and so on. The distal part of the inner layer pipe 151 has a window 127 formed as an opening for transmitting laser beams. The inner layer pipe 151 is totally covered, including its window 127, with an external tube 152 of a high laser transmission capability.

The distal end of the inner layer pipe 151 is attached with a cap 153. The cap 153 has a front observation window 154 for the forward view when the insertion unit 150 is inserted into the living body. The front observation window 154 has a light transmitting plate 155 with a good light transmitting capability embedded and affixed. The inside of the distal part of the insertion unit 150 is provided with a wall member 156 that defines the internal space. The wall member 156 has a pair of plate-like parts on the left and right sides.

The inside of the insertion unit 150 is provided with an optical fiber 107 for transmitting laser beams. The base end of the optical fiber 107 is connected to the laser generator 3 via an optical connector. This optical fiber 107 is covered entirely except its tip inside the insertion unit 150 by a protective pipe, for example, made of stainless steel for preventing it from breaking and bending. A fastening piece 157 affixed to the tip of the optical fiber 107 is rotatably attached to the mirror 123. A pipe 159 is inserted into a through hole 158 formed in the fastening piece 157. This allows the fastening piece 157 to slide along the pipe 159 in a stable manner. The pipe 159 also serves for supplying washing water through it. The flow of the washing water is deflected toward the front observation window 154 as it follows a flow passage 170 formed inside the cap 153 and washes the outside of the light transmitting plate 155.

Protrusions 131 provided on both sides of the front part of the base of the mirror 123 engage with and are supported slidably by a pair of grooves 129 formed on the wall member 156 in an angle relative to the axial direction of the insertion unit 150. The optical fiber 107 is driven and reciprocates in the axial direction of the insertion unit 150 by means of a driving device, i.e., motor 185 (refer to FIG. 7). When the optical fiber 107 itself is caused to reciprocate, the laser emission part 122 attached to the distal end of the optical fiber 107 changes the emitting angle continuously due to the function of the groove 129 as it reciprocates by means of transmitting the driving power by the optical fiber 107. Consequently, laser beams converge at a location 1000 located deep inside a tissue as shown in FIG. 2, only the location 1000 will be heated to a desired temperature for treatment, while areas other than the location 1000 will be held at lower temperatures.

The laser beam to be used does not have to be any specific kind and is acceptable as long as it has a sufficient depth reaching capability in the tissue. However, the wavelength of the laser beam should preferably be 750–1300 nm, or preferably 1600–1800 nm. The diameter of the insertion unit 150 of the laser irradiation unit 1 can be any size as long as it can be inserted into the intended body cavity. However, the diameter of the insertion unit 150 should preferably be 2–20 mm, or preferably 3–8 mm.

Coolant is circulated inside the insertion unit 150 in order to cool the surface of the tissue being irradiated with laser beams, the laser emission part 122 inside the insertion unit 150, etc. The coolant supplied via a water supply tube 105 flows through a lumen 160, then into a lumen 161 via a hole 163 in the vicinity of the distal end of the insertion unit 150, and discharged through a water drain tube 106. The coolant also flows into a lumen 162 as well through a hole 164 formed on the wall member 156.

An endoscope 501 is provided inside the insertion unit 150 as an observation member. The endoscope 501 is inserted from the proximal side of the laser irradiation unit 1 and is movable axially inside the insertion unit 150. The endoscope 501 has a suitable field of view for obtaining observation fields both from the window 127 and the front observation window 154. The endoscope 501 is not shown in FIG. 4 and FIG. 5, and the laser emission part 122 is not shown in FIG. 5.

The present embodiment provides a detection unit 165 that detects not only the reciprocating motion of the laser emission part 122 that contains the mirror 123 and detects the surface temperature of the tissue, which is to be thermally treated. The detection unit 165 is equipped with a reciprocating motion detection sensor 166 that detects the reciprocating motion of the laser emission part 122, and a urethra temperature sensor 167 for detecting the temperature of the urethra wall. The sensors 166 and 167 are installed in a storage area formed on the wall member 156. As shown in FIG. 5, the sensor can be installed using glue 169. Thermisters are used as the sensors 166 and 167. However, other temperature measuring sensors, such as thermocouples can be used as well. Also, the sensor 166 can be a sensor such as a photo-electronic device that is capable of detecting laser beams.

The reciprocating motion detection sensor 166 is provided in the vicinity of the proximal position in the reciprocating motion of the laser emission part 122, i.e., the vicinity of the read end of the window 127. This makes it possible, as shown in FIG. 2, to detect the laser beam emitted by the laser emission part 122 when the laser emission part 122 is at the proximal position (the position shown by solid lines in FIG. 2).

Figure 6:
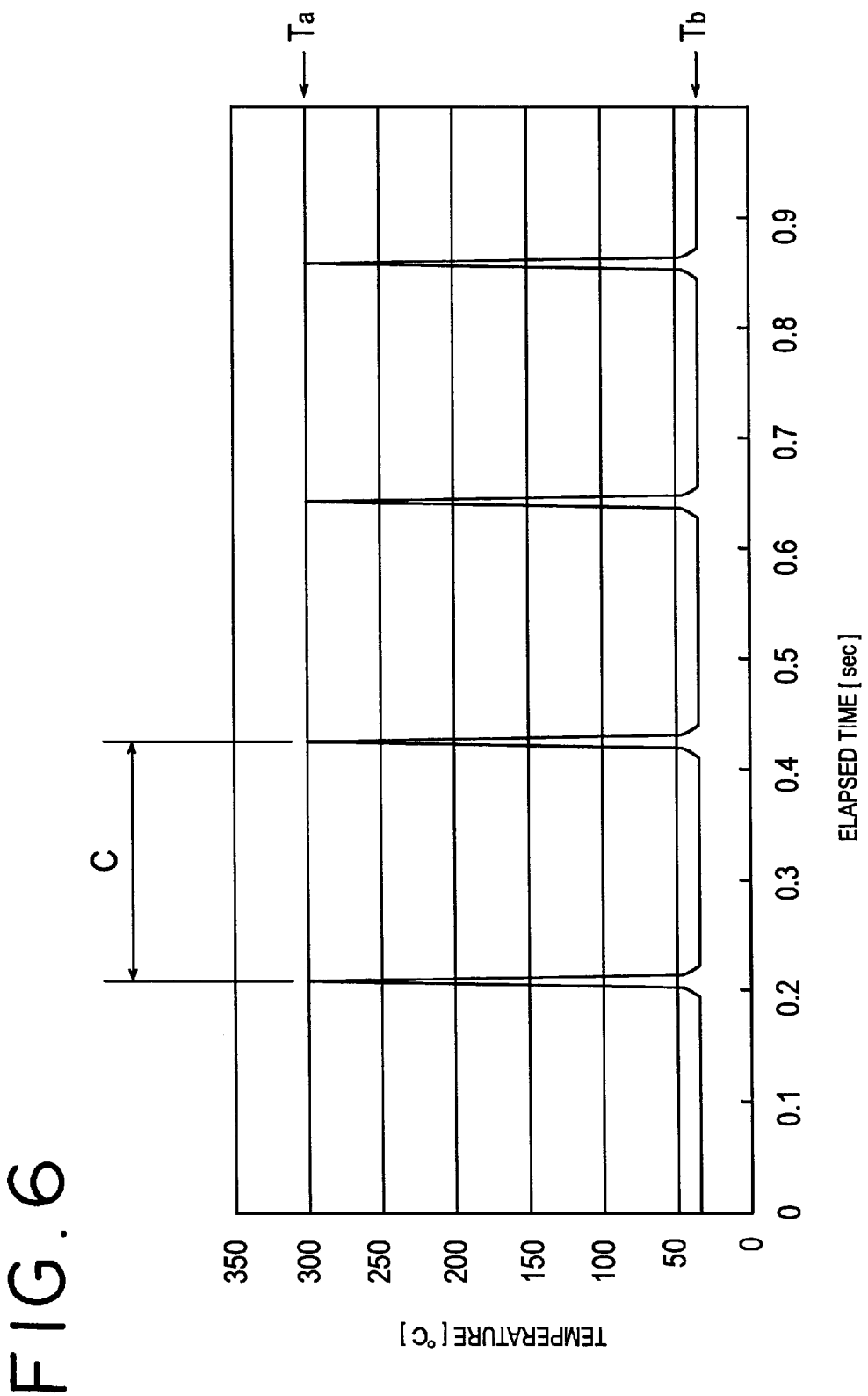
FIG. 6 is a graph showing values detected by the reciprocating motion detection sensor.

FIG. 6 is a graph showing values detected by the reciprocating motion detection sensor. The reciprocating motion detection sensor 166 issues a peak signal Ta instantly as shown in the diagram when it receives a laser beam emitted by the laser emission part 122. The reciprocating motion detection sensor 166 issues a low steady state signal Ta as shown in the diagram when it is not receiving laser beams. FIG. 6 shows the detection values obtained when the laser emission part 122 is reciprocating at the frequency of, e.g., 5 Hz, indicating that the peak signal Ta appears approximately every 0.2 seconds. The operating condition of the laser emission part 122 concerning the moving laser beam irradiation can be detected by checking the interval of the peak signal Ta detected by the reciprocating motion detection sensor 166, in other words checking the cycle C, etc.

On the other hand the urethra temperature sensor 167 will be placed in the vicinity of the middle side area of the window 127. This makes it possible to detect the temperature Tc of the urethra wall without disturbing the irradiation of the tissue with laser beams.

Figure 7:
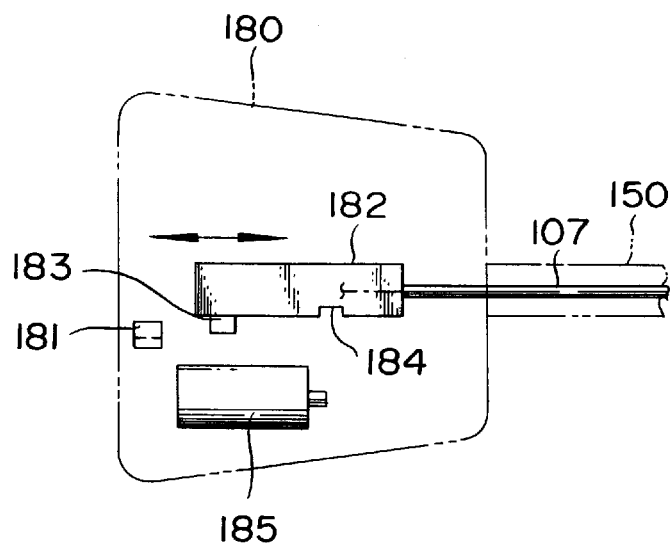
FIG. 7 is a diagrammatic view intended for describing the method of detecting that the laser emission part is at the rearmost position.

The present embodiment also provides an emission part position sensor 181, as shown in FIG. 7, such as a photo-interrupter that detects that the laser emission part 122 is at the proximal position (the position indicated by solid lines in FIG. 2). This emission part position sensor 181 is installed inside the proximal unit 180 of the laser irradiation unit 1. The emission part position sensor 181 can function as a position detection device for detecting the position of the laser emission part 122, or as a reciprocating motion detection device for detecting the reciprocating motion of the laser emission part 122. The protective cover covering the optical fiber 107, which is installed in the insertion unit 150, is fastened on an irradiating part slider 182. The irradiating part slider 182 is provided to be able to move in the arrowed direction inside the proximal unit 180, thus allowing the optical fiber 107 to move inside the insertion unit 150 as a result. The irradiating part slider 182 is connected to the motor 185, a drive unit, via a cam or a link mechanism (not shown) inside the proximal unit 180. The irradiating part slider 182 and the cam or the link mechanism are constituted removably by means of an engaging part 184. The cam or the link mechanism converts the rotating motion of the motor into a longitudinal reciprocating motion. Thus, as the motor runs, the irradiating part slider 182, the optical fiber 107, and the laser emission part 122 make a reciprocating motion in unison. A shutter 183 is provided on the irradiating part slider 182, and the emission part position sensor 181 detects the shutter 183 when the laser emission part 122 reaches the proximal position.

The emission part position sensor can be installed, for example, at a position where it can detect the laser emission part 122 itself, or the fastening member 157 to which the laser emission part 122 of the distal side of the protective pipe that covers the optical fiber 107 is attached. The emission part position sensor can be a limit switch or any other type of sensor.

The detected signals from the reciprocating motion detection sensor 166, the urethra temperature sensor 167, and the emission part position sensor 181 mentioned above are transmitted to the main controller 2 via a urethra probe cable 104.

The proximal end of the optical fiber 107 is connected to the laser generator 3. The proximal end of the urethra probe cable 104 is connected to the main controller 2. The water supply tube 105 and the water drain tube 106 are connected to a coolant circulation unit (not shown) located inside behind the cooling unit door 201 of the main controller 2.

The rectum probe 4 is equipped with a rectum temperature sensor (not shown). As the rectum probe 4 is inserted into the rectum, the rectum temperature sensor is resultantly placed at a deeper part of the prostate relative to the urethra without having to be implanted into the tissue. The signal detected by the rectum temperature sensor is transmitted to the main controller 2 via a rectum probe cable 401.

The endoscope system 5 is equipped with a light source 505 for supplying an illuminating light for endoscope observation, a TV camera 506 for importing the image observed by the endoscoped, and a video receiver 507 for displaying images imported into the TV camera 506. The light source 505 is connected to a light guide 502. The TV camera 506 is connected to a camera head 503 via a camera signal lead wire 504. This makes it possible to apply thermal treatment while observing through the endoscope 501.

A guide lumen 171 is formed inside the insertion unit 150 of the laser irradiation unit 1 for supporting the endoscope 501 for allowing it to travel in the moving direction of the laser emission part 122, in other words, the longitudinal direction of the inserting part 150.

Figure 8:
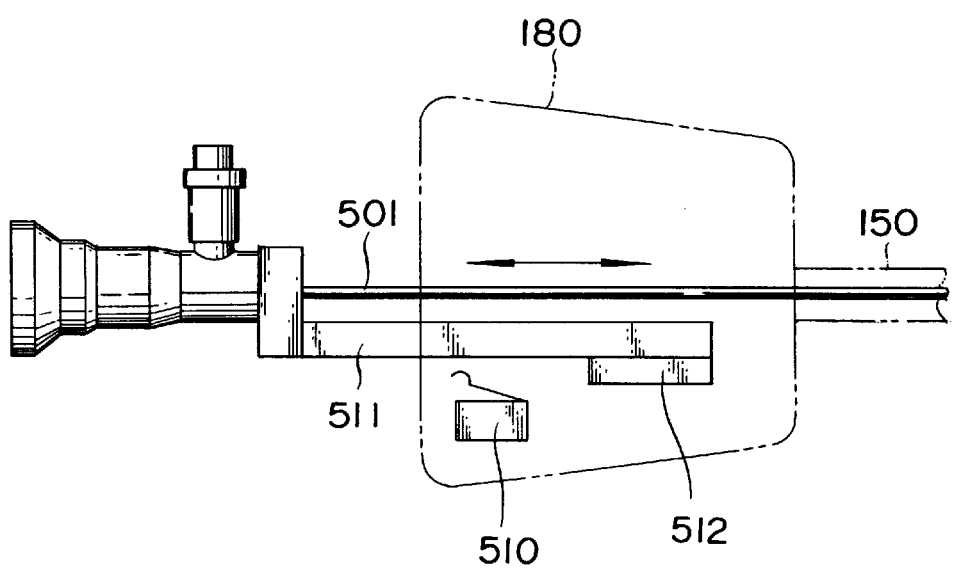
FIG. 8 is a diagrammatic view intended for describing the method of detecting the movement of the endoscope.

The present embodiment provides an endoscope motion detection sensor 510 as shown in FIG. 8 as a motion detection device such as a limit switch for detecting the motion of the endoscope 501. This endoscope motion detection sensor 510 is installed inside the proximal unit 180 of the laser irradiation unit 1. The endoscope 501 is affixed to a slide lever 511 and an endoscope slider 512 is affixed to the distal part of the slide lever 511. The endoscope slider 512 is provided in such a way as to be able to travel in the arrowed direction in the traveling space restricted by the case member (not shown). The endoscope 501 resultantly is allowed to travel inside the insertion unit 150 between the position shown in FIG. 2 and the position immediately ahead of the forward observation window 154. When the endoscope slider 512 reaches the proximal end, in other words, the endoscope 501 is pulled out to the proximal end, the lever of the endoscope motion detection sensor 510 makes a contact with the endoscope slider 512, which turns on the sensor 510. The endoscope motion detection sensor 510 can be other kinds of sensor such as an optical sensor.

The main controller 2 controls the motions of the entire thermal treatment apparatus using various detection sensors provided on the laser irradiation unit 1 and the rectum probe 4. For example, by detecting the temperature of the urethra wall by means of the urethra temperature sensor 167, the main controller 2 is capable of controlling and preventing the normal tissue of the urethra from being heated unnecessarily.

A user interface 207 is provided in the upper part of the main controller 2 for displaying various kinds of information for the benefits of the user and for accepting various setups and operations. The user interface 207 of the present embodiment is a touch screen unit. The communication cable 206 is for exchanging signals between the laser generator 3 and the main controller 2.

Figure 9:
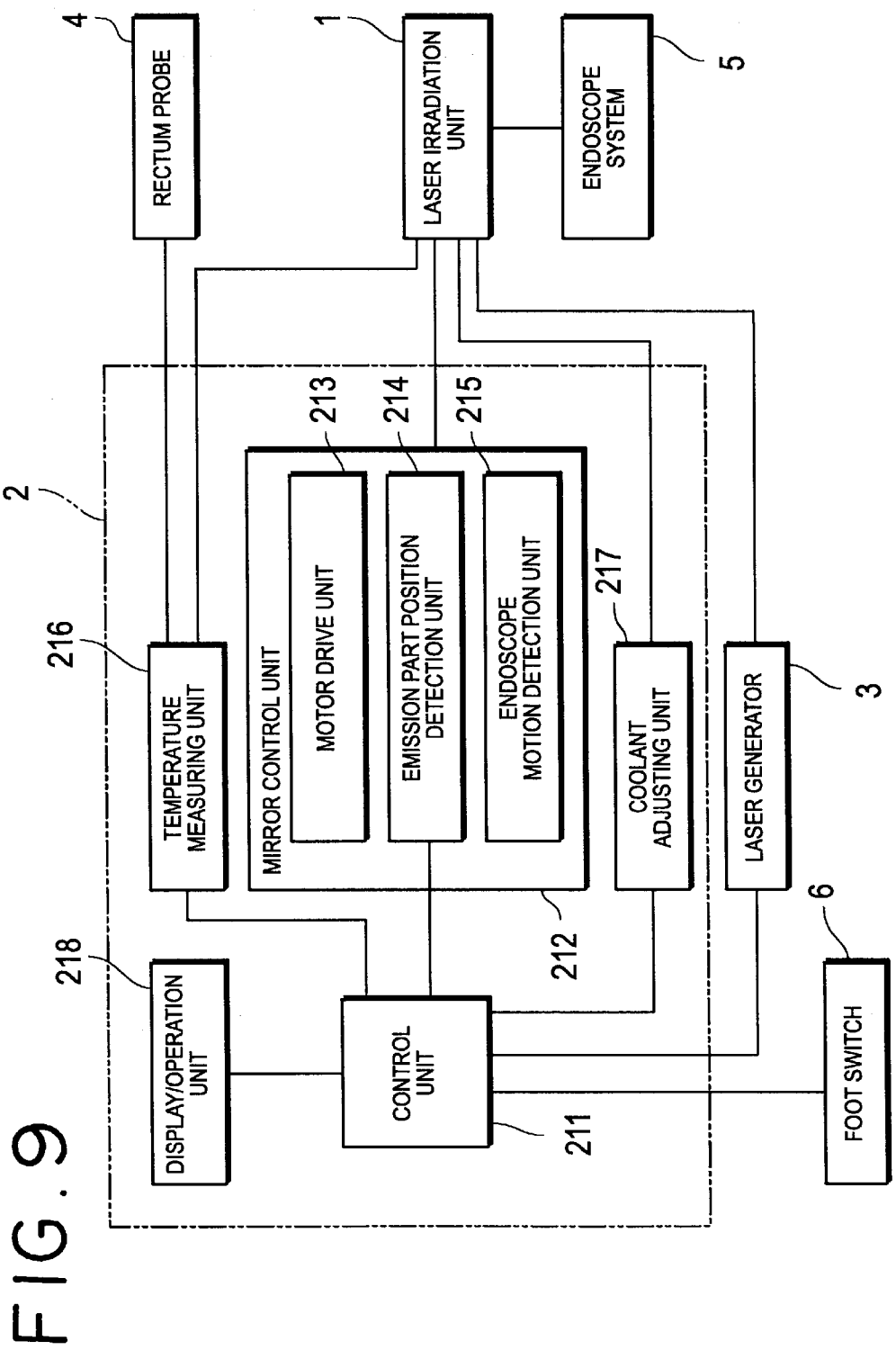
FIG. 9 is a general control system block diagram for the thermal treatment apparatus.

FIG. 9 is a general control system block diagram for the thermal treatment apparatus.

The main controller 2 of the thermal treatment apparatus has a control unit 211 in charge of overall control of various parts. The control unit 211 is connected to various peripheral control units such as a mirror control unit 212, a temperature measuring unit 216, a coolant adjusting unit 217, and a display/operation unit 218. The control unit 211 is further connected to the laser generator 3 and the foot switch 6.

The mirror control unit 212 is connected to the laser irradiation unit 1, and exchanges signals with the laser irradiation unit 1 concerning the reciprocating motion of the laser emission part 122. The mirror control unit 212 is equipped with a motor drive unit 213, an emission part position detection unit 214, and an endoscope motion detection unit 215. The motor drive unit 213 is connected to the motor 185 for moving the laser emission part 122 and controls the operation of the motor 185. The emission part position detection unit 214 receives signals from the emission part position sensor 181 and the reciprocating motion detection sensor 166, while the endoscope motion detection unit 215 receives signals from the endoscope motion detection sensor 510.

The temperature measuring unit 216 receives signals from the urethra temperature sensor 167 of the laser irradiation unit 1 and also the rectum temperature sensor of the rectum probe 4. The coolant adjusting unit 217 receives signals from various sensors provided on the coolant circulation unit (not shown) for detecting temperatures, pressures, flow rates, etc. The display/operation unit 218 exchanges signals with the user interface 207.

Figure 10:
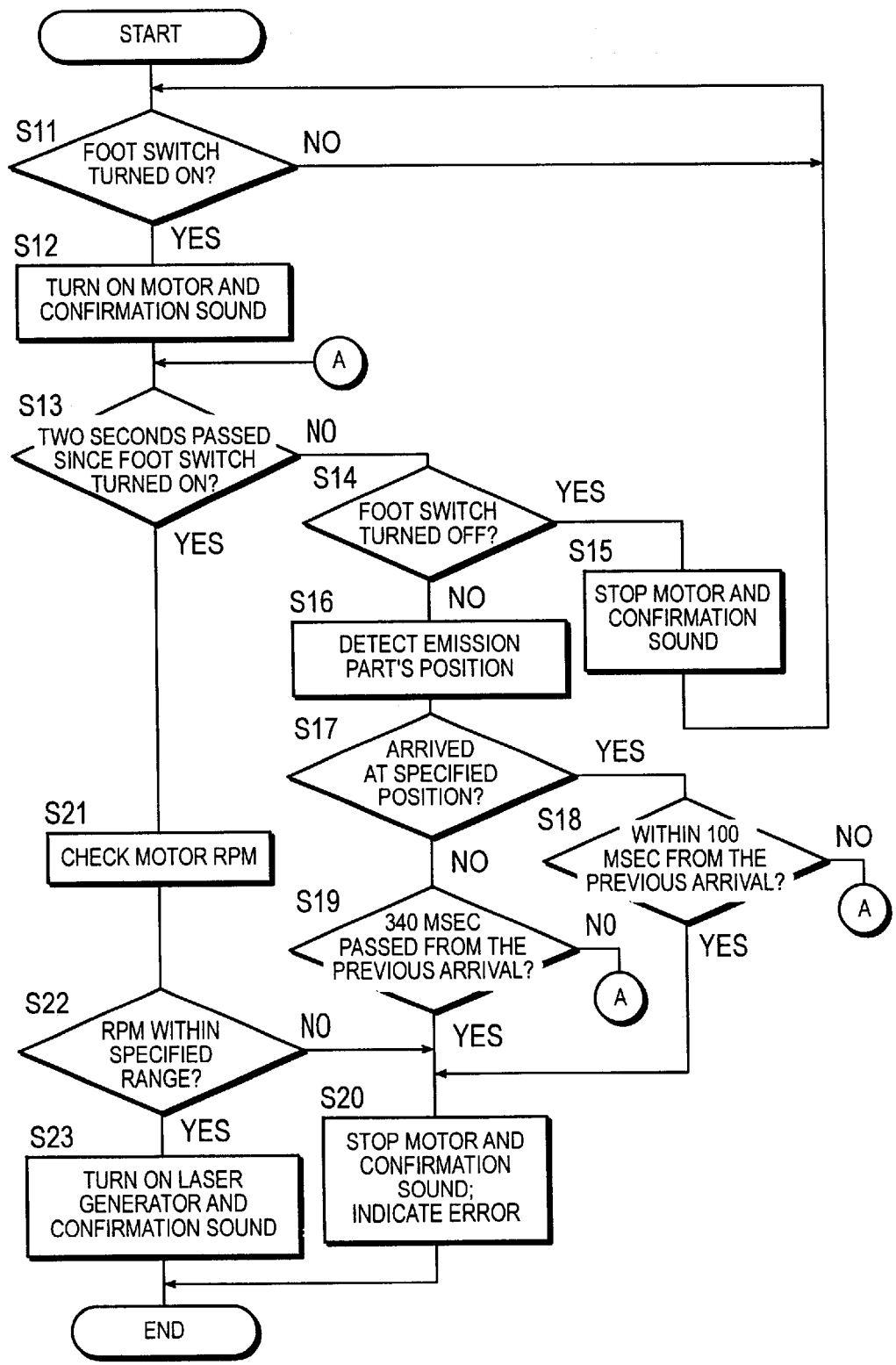
FIG. 10 is a flowchart indicating the control sequence for the moving laser beam irradiation at the start of laser irradiation of the thermal treatment apparatus according to the first embodiment.
Figure 11:
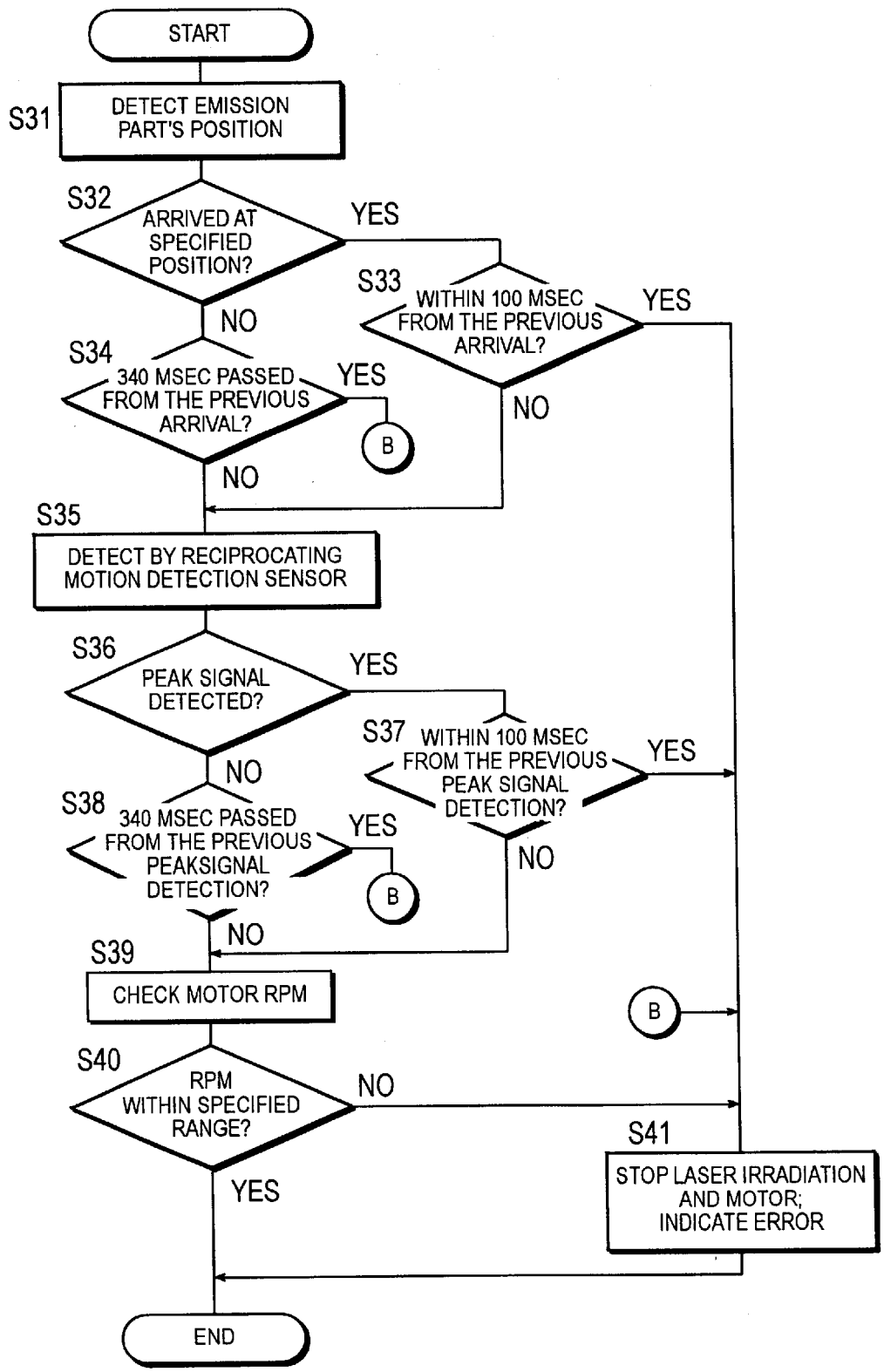
FIG. 11 is a flowchart indicating the control sequence for the moving laser beam irradiation during laser irradiation of the thermal treatment apparatus according to the first embodiment.
Figure 12:
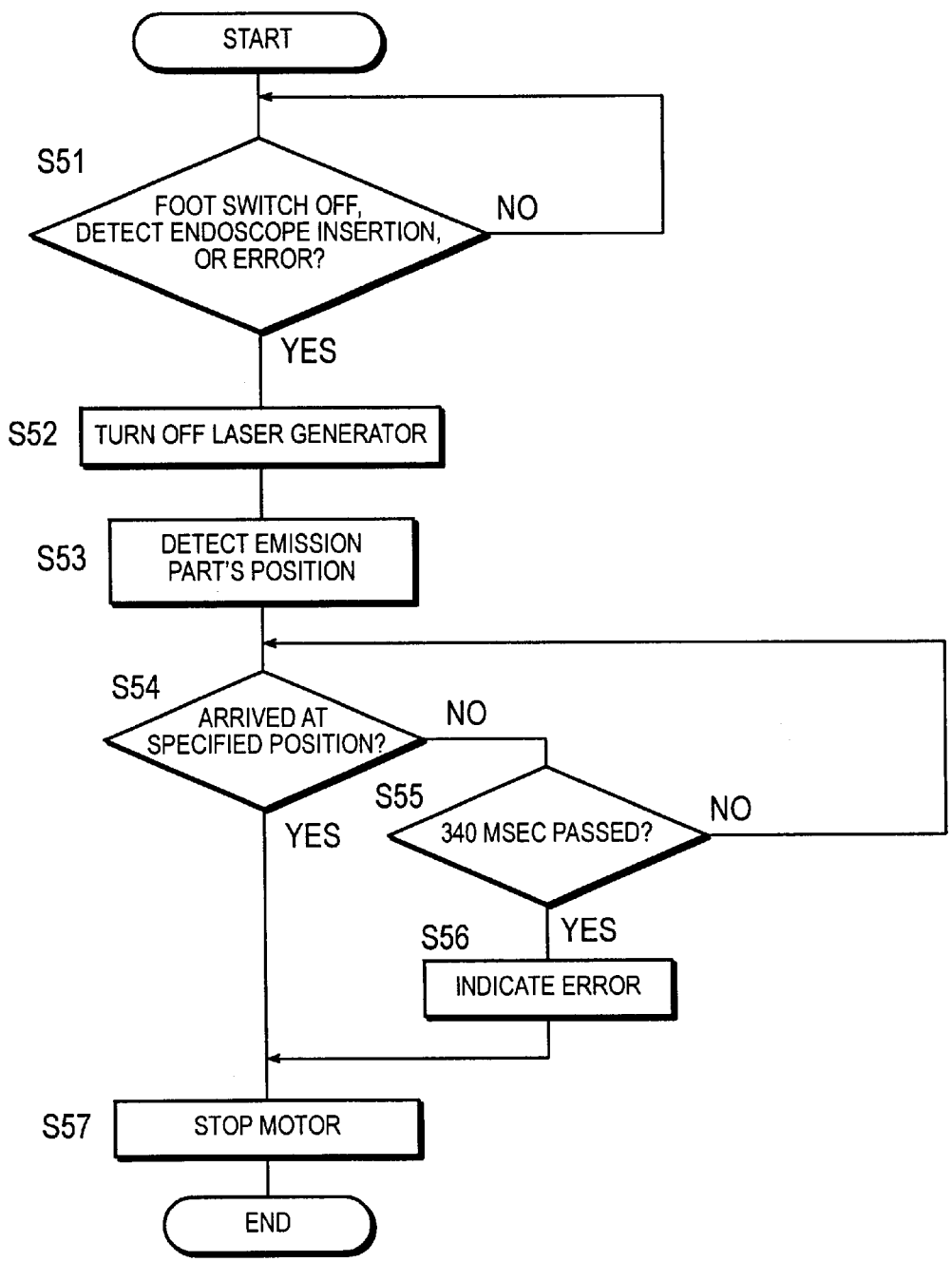
FIG. 12 is a flowchart indicating the control sequence for the moving laser beam irradiation at the termination of laser irradiation of the thermal treatment apparatus according to the first embodiment.

FIG. 10 through FIG. 12 are flowcharts indicating the control sequences for the moving laser beam irradiation of the thermal treatment apparatus according to the present embodiment.

First, the control sequence for the moving laser beam irradiation at the start of laser emission will be described referring to FIG. 10.

When the foot switch 6 is turned on (S11: Yes), the system turns on the motor 185 for moving the laser emission part 122 and issues a confirmation sound notifying that the motor is operating (S12). Next, a judgment is made whether a specified time (e.g., 2 seconds) has passed after the foot switch 6 is turned on (S13). If the foot switch 6 is turned off (S14: Yes) before the specified time has passed since the foot switch 6 was turned on (S13: No), the motor rotation stops and the confirmation sound will be stopped (S15).

If the specified time has not passed since the foot switch 6 was turned on (S13: No), and the foot switch is not turned off (S14: No), the emission part position sensor 181 detects the position of the laser emission part 122 (S16) to detect if the laser emission part 122 has arrived at the proximal position, which is its reference position (S17). Then, the time interval between each time when the laser emission part 122 arrives at the proximal position repeatedly due to its reciprocating motion. Here, the arrival of the laser emission part 122 at its proximal position means the change of the status of the laser emission part 122 from a position different from the proximal position to the proximal position. This makes it possible to detect a case when the laser emission part 122 stops at the proximal position.

If a new arrival of the laser emission part 122 at the proximal position is detected (S17: Yes), and it happens to be within 100 msec from the last arrival (S18: Yes), the system judges that the traveling speed of the laser emission part 122 is too fast, i.e., the cycle of the reciprocating motion is too short, stops the motor and the confirmation sound, and displays a specified error indication (S20). On the other, if a new arrival of the laser emission part 122 at the proximal position is not detected (S17: No), and it has been more than 340 msec since the last arrival (S19: Yes), the system judges that the traveling speed of the laser emission part 122 is too slow, i.e., the cycle of the reciprocating motion is too long, stops the motor and the confirmation sound, and displays a specified error indication (S20). As a result, if the time interval C (msec) between each time when the laser emission part 122 arrives at the proximal position repeatedly due to its reciprocating motion is within the range represented by, for example, 100<C<340, the system judges that the reciprocating motion of the laser emission part 122 is correct.

The procedure of confirming the operation indicated by the steps S14 through S20 is repeated for 2 seconds after the foot switch 6 is turned on. If the motor and the confirmation sound do not stop during this period (S13: Yes), the motor rpm will be detected by a sensor such as an encoder (S21). If the motor speed is within the specified range (S22: Yes), the laser generator 3 starts to generate the laser beam, and the laser confirmation sound is issued (S23).

Therefore, it is possible to avoid the laser beam from being continuously emitted when the traveling motion of the laser emission part 122 is incorrect by checking the reciprocating motion of the laser emission part 122 for a specified period before emitting the laser.

Moreover, the reciprocating motion of the laser emission part 122 and the laser emission can be activated sequentially by operating the foot switch 6 alone. Furthermore, even if the foot switch 6 is turned on erroneously, the laser emission can be cancelled before it starts to emission as it is not started immediately.

Next, the control sequence for the moving laser beam irradiation during laser emission will be described referring to FIG. 11.

During the laser emission, the emission part position sensor 181 detects the position of the laser emission part 122 (S31), and a judgment is made as to whether the laser emission part 122 has arrived at the proximal position, which is its reference position (S32). If a new arrival of the laser emission part 122 at the proximal position is detected (S32: Yes), and it happens to be within 100 msec since the last arrival (S33: Yes), the system judges that the traveling speed of the laser emission part 122 is too fast, stops the laser beam emission and the motor rotation, and displays a specified error indication (S41). If a new arrival of the laser emission part 122 at the proximal position is not detected (S32: No), and it happens to be within 340 msec since the last arrival (S34: Yes), the system judges that the traveling speed of the laser emission part 122 is too slow, stops the laser beam emission and the motor rotation, and displays a specified error indication (S41).

If the time interval C (msec) between each time when the laser emission part 122 arrives at the proximal position repeatedly due to its reciprocating motion is within the range represented by, for example, 100<C<340, the system checks the output value of the reciprocating motion detection sensor 166 (S35) and makes a judgment as to whether the peak signal Ta (see FIG. 6) has been detected (S36). If it is confirmed by the reciprocating motion detection sensor 166 that the laser emission part 122 is at the proximal position, the laser beam itself emitted by the laser emission part 122 is detected.

If a new peak signal is detected by the reciprocating motion detection sensor 166 (S36: Yes), and it happens to be within 100 msec since the last peak signal detection (S37: Yes), the system judges that the traveling speed of the laser emission part 122 is too fast, stops the laser beam emission and the motor rotation, and displays a specified error indication (S41). On the other hand, if a new peak signal is not detected by the reciprocating motion detection sensor 166 (S36: No), and it has been more than 340 msec since the last peak signal detection (S38: Yes), the system judges that the traveling speed of the laser emission part 122 is too slow, stops the laser beam emission and the motor rotation, and displays a specified error indication (S41).

At the step S39, the motor rpm is detected by a sensor such as an encoder (S39). If the motor rpm is not within the specified range (S40: No), the system stops the laser emission and the motor rotation, and displays a specified error indication (S41). During the laser emission, the sequences shown in the flowchart of FIG. 11 are repeated.

Therefore, it is possible to avoid the laser beam from being continuously emitted when the traveling motion of the laser emission part 122 is incorrect by checking the reciprocating motion of the laser emission part 122 continuously while the laser beam emission. Moreover, if the laser beam itself emitted by the laser emission part 122 is detected by the reciprocating motion detection sensor 166, it is possible to confirm simultaneously that the laser beam is being emitted.

Next, the control sequence for the moving laser beam irradiation while the laser beam emission is at a halt will be described referring to FIG. 12.

The laser emission will be stopped immediately, if the laser irradiation stop instruction is issued by means of turning off the foot switch 6, or if the insertion of the endoscope 501 into the distal part of the insertion unit 150 is detected, or if the temperature detected by the urethra temperature sensor 167 is out of limits of the preset range, or if the detected temperature of the coolant is out of limits of the preset range (S51: Yes) during the laser emission (S52).

Next, the emission part position sensor 181 detects the position of the laser emission part 122 (S53), and a judgment is made as to whether the laser emission part 122 has arrived at the proximal position, which is its reference position (S54). When the laser emission part 122 arrives at the proximal position (S54: Yes), the motor will be stopped (S57). In other words, the laser emission part 122 is positioned and stopped at the proximal position when the laser irradiation is stopped.

On the other hand, if 340 msec have passed (S55: Yes) without the laser emission part 122 having arrived at the proximal position (S54: No), an error indication will be displayed (S56), and the motor will be stopped (S57).

Therefore, by confirming that the laser emission part 122 has moved to the proximal position and stopped when the laser emission is at a halt, it is possible to avoid the next operation from starting while the movement of the laser emission part 122 is in an improper state.

Moreover, when the laser emission part 122 is stopped at the proximal position, the mirror 123 is positioned at the upper position of the inside of the insertion unit 150 on FIG. 2 and most closely tilted toward the horizontal direction in FIG. 2. Consequently, it is possible to move the endoscope 501 to the distal part of the insertion unit 150 without interfering with the mirror 123, thus facilitating the forward and side observations with the endoscope 501.

As can be seen from the above, the first embodiment of the present invention makes it possible to irradiate the target lesion with laser beams accurately to achieve excellent treatment effects by securing preferable reciprocating motion and stopping operation of the laser emission part.

In particular, when it stops during the reciprocation motion, the laser emission part 122 stops at a position where it doesn't interfere with the motion passage of the endoscope. Therefore, it is possible to move the endoscope 501 toward the distal part of the insertion unit 150 without interfering with the mirror 123, so that it is possible to facilitate the observation with the endoscope 501. Furthermore, even if the endoscope is moved to the distal part of the insertion unit, there is no danger of damaging the laser emission part 122 or the endoscope 501. Furthermore, it is possible to make sure for the laser emission part 122 to make proper reciprocating motion and stopping operation by directly monitoring the reciprocating motion of the laser emission part 122 in addition to the monitoring of the motion of the motor 185.

Also, since the laser emission part 122 will be stopped when the movement of the endoscope 501 toward the distal side is detected, the endoscope 501 will be prevented from colliding against the moving laser emission part 122.

Moreover, even after the laser emission start instruction is made, laser emission begins only when the laser emission part 122 is reciprocated and the result of detecting the reciprocating motion meets a certain set condition within a certain time. Therefore, it is possible to avoid the laser beam from being started when the traveling motion of the laser emission part 122 is incorrect. Moreover, the reciprocating motion of the laser emission part 122 and the laser emission can be activated sequentially by operating the foot switch 6 alone; furthermore, even if the foot switch 6 is turned on erroneously, the laser emission can be cancelled before it starts to emission.

Figure 13:
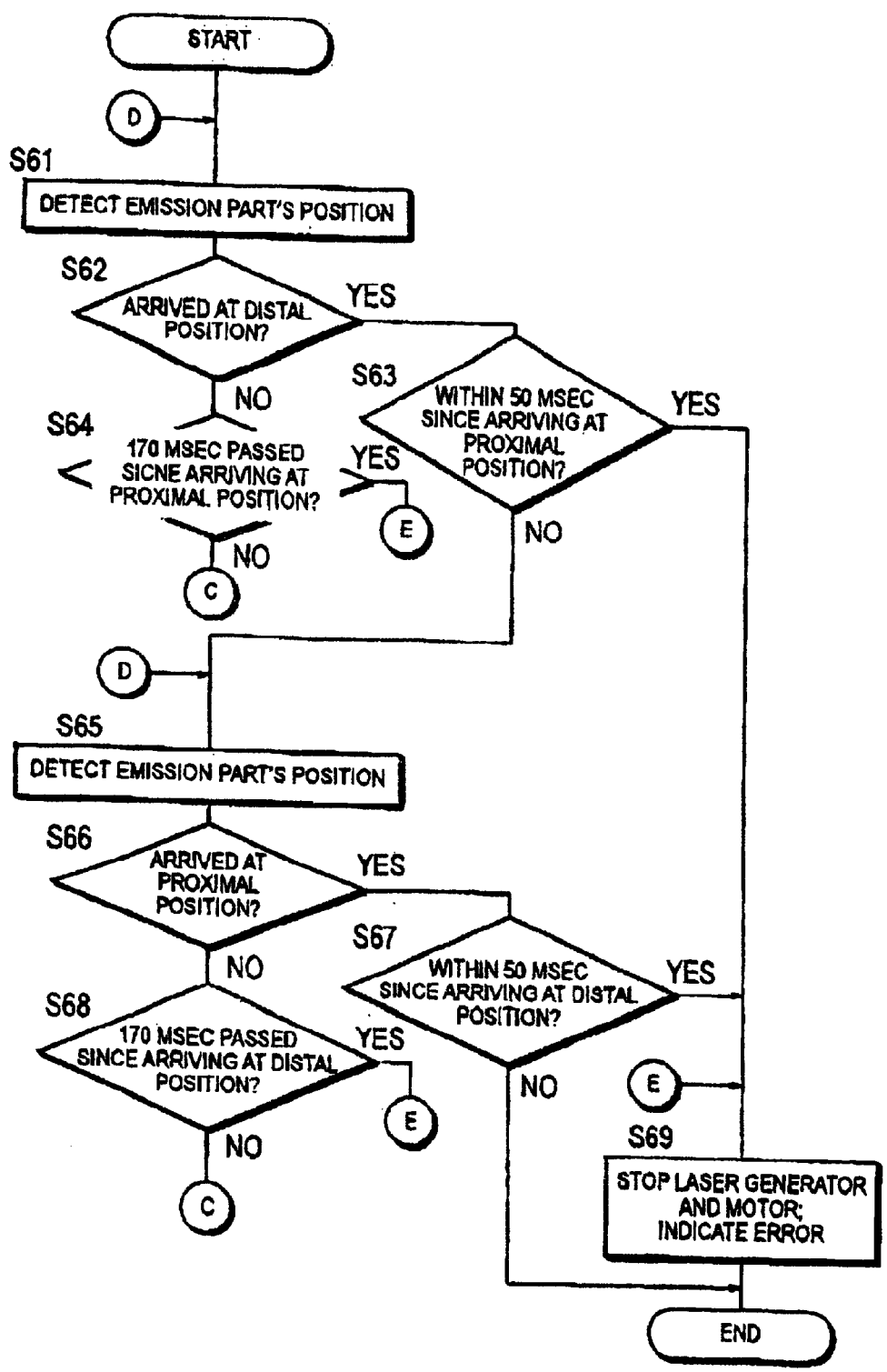
FIG. 13 is a flowchart indicating the control sequence for the moving laser beam irradiation of the thermal treatment apparatus according to a second embodiment.
Figure 14:
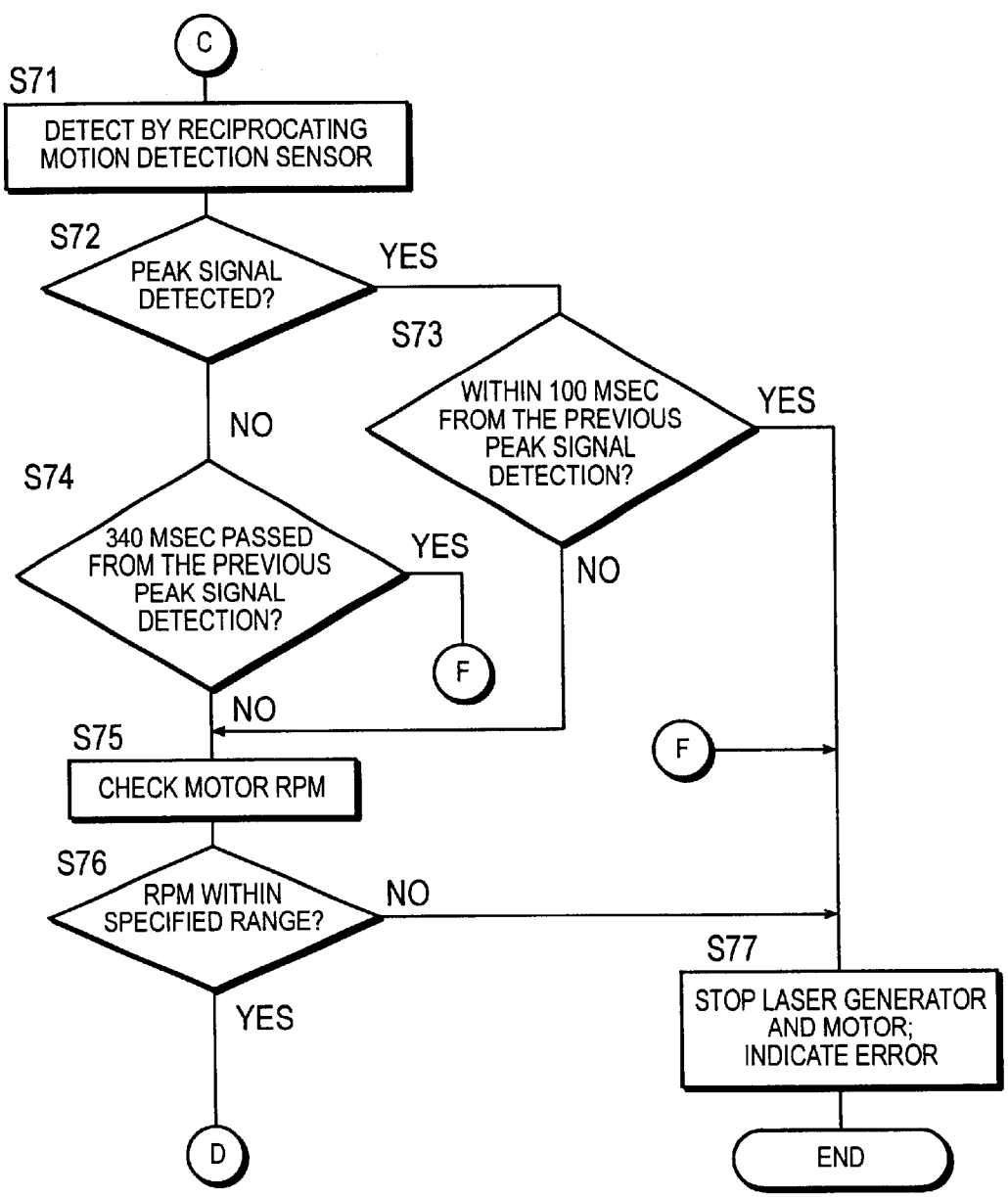
FIG. 14 is a flowchart indicating the control sequence for the moving laser beam irradiation of the thermal treatment apparatus according to the second embodiment.

[Embodiment 2] FIG. 13 and FIG. 14 are flowcharts indicating the control sequence for the moving laser beam irradiation of the thermal treatment apparatus according to a second embodiment. The second embodiment will be described bellow primarily concerning with the differences from the first embodiment while omitting descriptions on common parts.

The second embodiment is different from the first embodiment in that it has, in addition to the emission part position sensor 181 that detects that the laser emission part 122 is located at the proximal position (position indicated by solid lines in FIG. 2), another emission part position sensor (not shown), e.g., a photo-interrupter, which detects that the laser emission part 122 is located at the distal position (the one on the right side of the two positions indicated by phantom lines in FIG. 2), is provided in the proximal unit 180. Other constitutions of the thermal treatment apparatus of this embodiment are identical to those of the first embodiment. The reciprocating motion of the laser emission part 122 in the second embodiment is detected by detecting the time interval between each detection result by the two emission part position sensors provided on the distal side and the proximal side.

Next, the control sequence for the moving laser beam irradiation during laser emission will be described referring to FIG. 13 and FIG. 14. As to the control procedures concerning the moving laser beam irradiation at the start of the laser irradiation and at the time when the laser beam irradiation is stopped are identical to those in the first embodiment.

During the laser emission, the two laser emission part position sensors provided at the distal side and the proximal side detect the position of the laser emission part 122 (S61). If the laser emission part 122 arrives at the distal position (S62: Yes), and it happens to be within 50 msec since the last arrival at the proximal position (S63: Yes), the system judges that the traveling speed of the laser emission part 122 is too fast, stops the laser beam emission and the motor rotation, and displays a specified error indication (S69). On the other hand, if a new arrival of the laser emission part 122 at the distal position is not detected (S62: No), and it has been more than 170 msec since the last arrival at the proximal position (S64: Yes), the system judges that the traveling speed of the laser emission part 122 is too slow, stops the laser beam emission and the motor rotation, and displays a specified error indication (S69).

If it is judged No (negative) in the step S63, the two laser emission part position sensors provided at the distal side and the proximal side detect the position of the laser emission part 122 (S65). If the laser emission part 122 arrives at the proximal position (S66: Yes), and it happens to be within 50 msec since the last arrival at the distal position (S67: Yes), the system judges that the traveling speed of the laser emission part 122 is too fast, stops the laser beam emission and the motor rotation, and displays a specified error indication (S69). On the other hand, if the arrival of the laser emission part 122 at the proximal position is not detected (S66: No), and it has been more than 170 msec since the last arrival at the distal position (S68: Yes), the system judges that the traveling speed of the laser emission part 122 is too slow, stops the laser beam emission and the motor rotation, and displays a specified error indication (S69).

Also, if it is judged No (negative) in the step S64 or the step S68, the process shown in FIG. 14 will be executed. Since the steps S71 through S77 shown in FIG. 14 are identical to the steps S35 through S41 shown in FIG. 11, the descriptions are omitted. When executing the process shown in FIG. 14 following the step S64 shown in FIG. 13, it advances to step S61 of FIG. 13 if it is judged Yes (affirmative) in the step S76 of FIG. 14; when executing the process shown in FIG. 14 following the step S68 shown in FIG. 13, it advances to step S65 if it is judged Yes (affirmative) in the step S76 of FIG. 14. During the laser emission, the sequences shown in the flowchart of FIG. 13 and FIG. 14 are repeated.

As can be seen from the above, the second embodiment not only provides the same effect as in the first embodiment, but also makes it possible to detect the operating condition of the laser emission part 122 for each stroke even in a case when different moving speeds are set for the forward stroke and the backward stroke of the reciprocating motion. Moreover, it makes it possible to detect whether the operation of the laser emission part 122 is proper more quickly.

Figure 15:
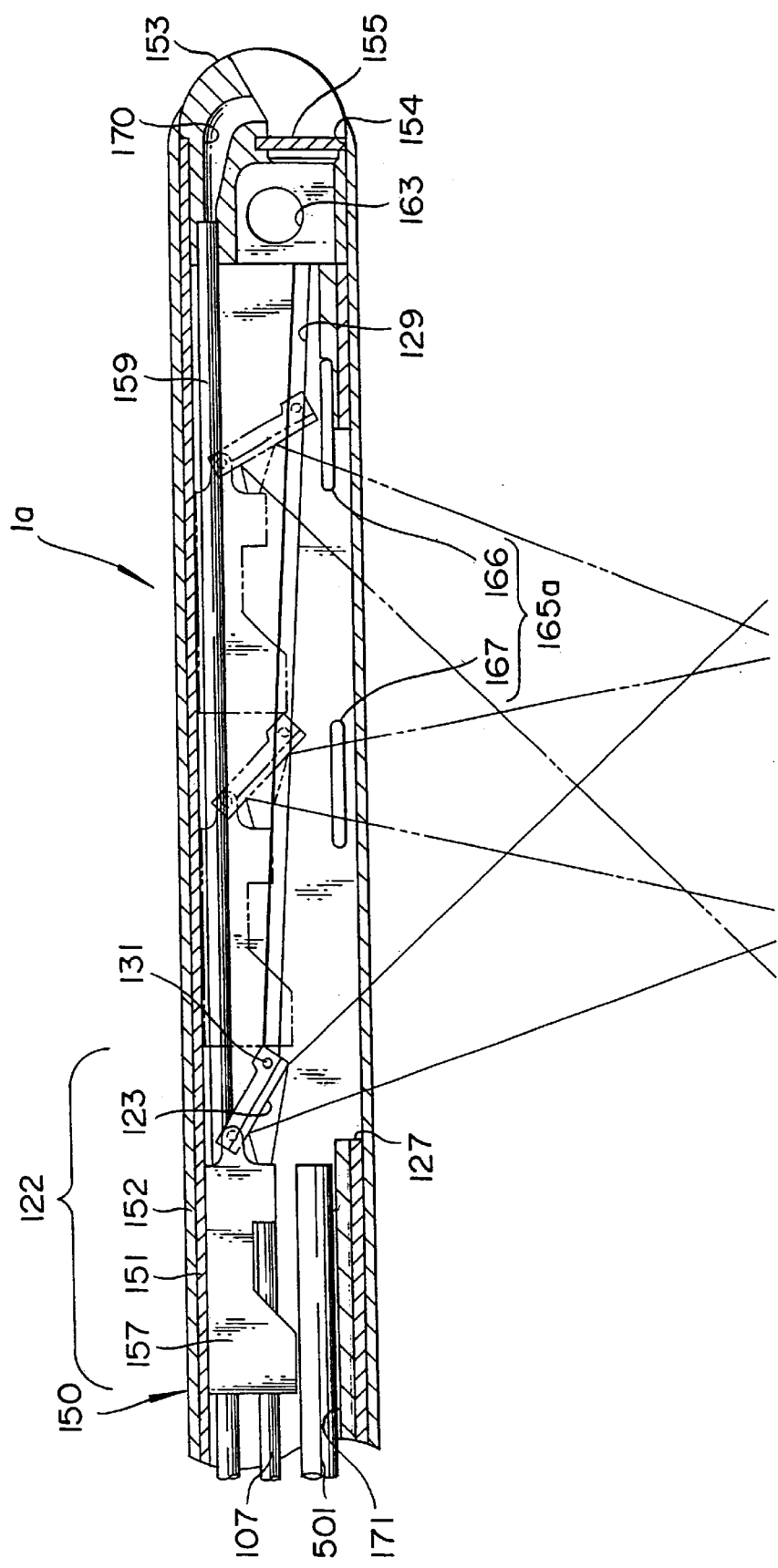
FIG. 15 is a cross sectional view of the distal part of the laser irradiation unit used on a thermal treatment according to a third embodiment.
Figure 16:
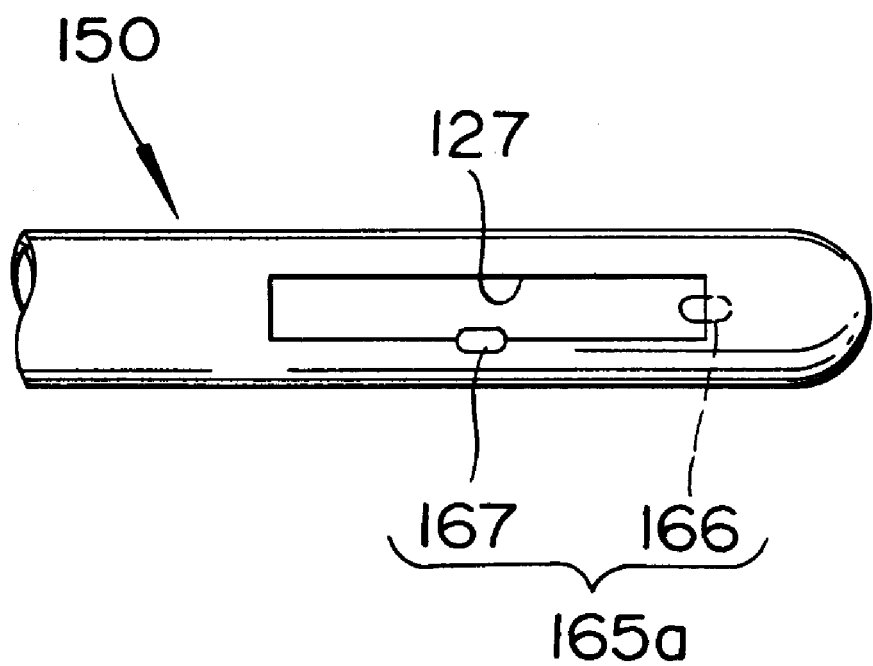
FIG. 16 is a schematic bottom view of FIG. 15.

[Embodiment 3] FIG. 15 is a cross sectional view of the distal part of the laser irradiation unit used on a thermal treatment according to a third embodiment and FIG. 16 is a schematic bottom view of FIG. 15. The third embodiment will be described bellow primarily concerning with the differences from the first embodiment while omitting descriptions on common parts.

The laser irradiation unit 1*a* of the third embodiment is different from that of the first embodiment in that the reciprocating motion detection sensor 166 of the detection unit 165*a* is located in the vicinity of the distal position of the reciprocating motion of the laser emission part 122, i.e., the vicinity of the front end of the window 127. This makes it possible, as shown in FIG. 15, to detect the laser beam emitted by the laser emission part 122 when the laser emission part 122 is at the distal position (the right side one of the two positions shown by phantom lines in FIG. 15). Other constitutions of the thermal treatment apparatus of this embodiment are identical to those of the first embodiment. The third embodiment detects the reciprocating motions of the laser emission part 122 by means of time intervals calculated from the detections of the reciprocating motion sensor 166 and the emission part position sensor 181.

Figure 17:
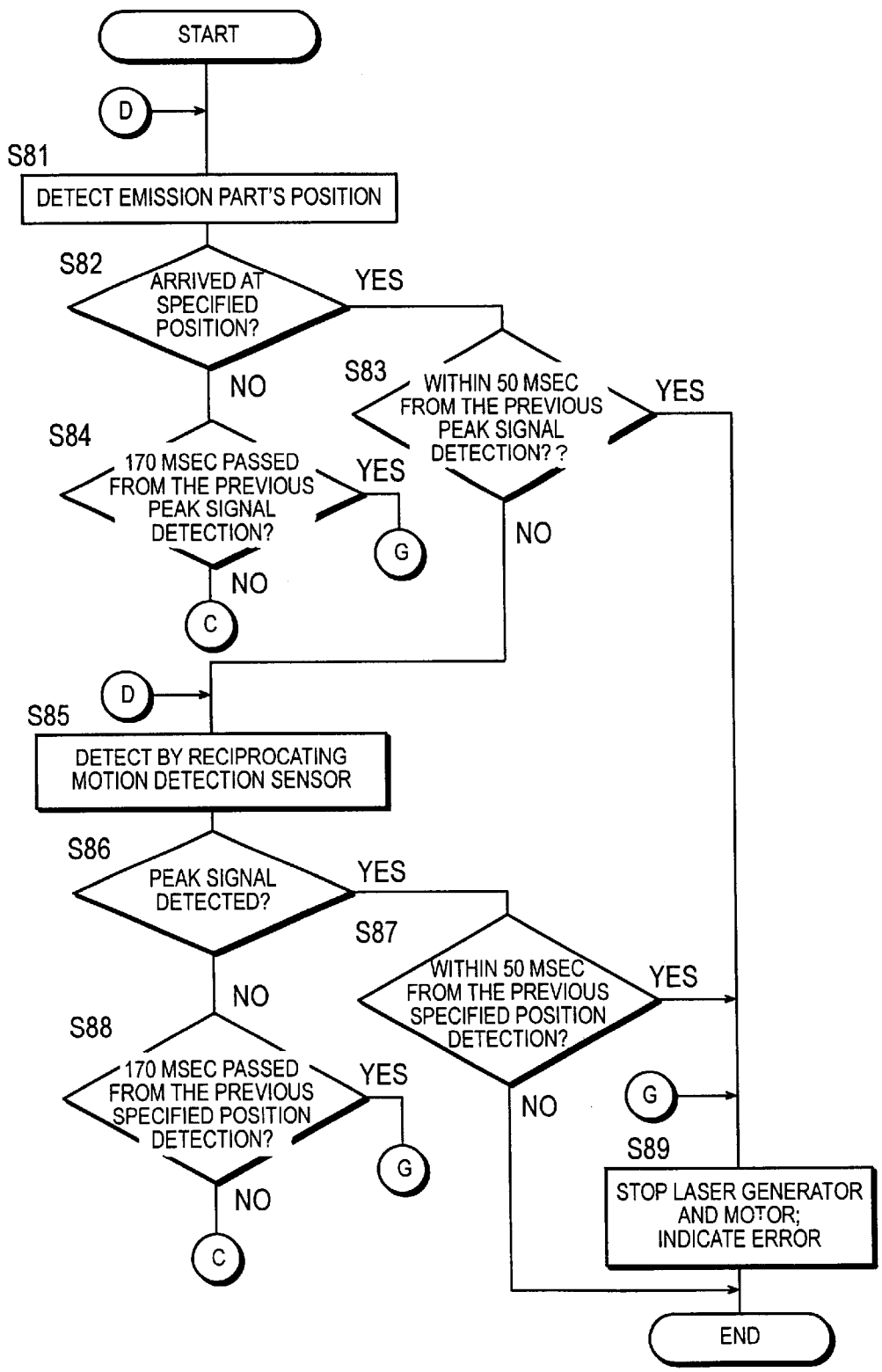
FIG. 17 is a flowchart indicating the control sequence for the moving laser beam irradiation of the thermal treatment apparatus according to the third embodiment.

FIG. 17 is a flowchart indicating the control sequence for the moving laser beam irradiation of the thermal treatment apparatus according to the third embodiment.

First, the control sequence for the moving laser beam irradiation during laser emission will be described referring to FIG. 17. As to the control procedures concerning the moving laser beam irradiation at the start of the laser irradiation and at the time when the laser beam irradiation is stopped are identical to those in the first embodiment. During the laser emission, the emission part position sensor 181 detects the position of the laser emission part 122 (S81), and a judgment is made as to whether the laser emission part 122 has arrived at the proximal position, which is its reference position (S82). If a new arrival of the laser emission part 122 at the proximal position is detected (S82: Yes), and it happens to be within 50 msec since the last peak signal detection by the reciprocating motion detection sensor 166 (S83: Yes), the system judges that the traveling speed of the laser emission part 122 is too fast, stops the laser beam emission and the motor rotation, and displays a specified error indication (S89). On the other hand, if a new arrival of the laser emission part 122 at the proximal position is not detected (S82: No), and it has been more than 170 msec since the last peak signal detection by the reciprocating motion detection sensor 166 (S84: Yes), the system judges that the traveling speed of the laser emission part 122 is too slow, stops the laser beam emission and the motor rotation, and displays a specified error indication (S89).

If it is judged No (negative) in the step S83, the system checks the output value of the reciprocating motion detection sensor 166 (S85), and makes a judgment as to whether the peak signal Ta (see FIG. 6) has been detected (S86). If it is confirmed by the reciprocating motion detection sensor 166 that the laser emission part 122 is at the distal position, the laser beam itself emitted by the laser emission part 122 is detected.

If a new peak signal is detected by the reciprocating motion detection sensor 166 (S86: Yes), and it happens to be within 50 msec since the last arrival at the proximal position is detected by the emission part position detection sensor 181 (S87: Yes), the system judges that the traveling speed of the laser emission part 122 is too fast, stops the laser beam emission and the motor rotation, and displays a specified error indication (S89). If a new peak signal is not detected by the reciprocating motion detection sensor 166 (S86: No), and it has been more than 170 msec since the last arrival at the proximal position is detected by the emission part position detection sensor 181 (S88: Yes), the system judges that the traveling speed of the laser emission part 122 is too slow, stops the laser beam emission and the motor rotation, and displays a specified error indication (S89).

Also, if it is judged No (negative) in the step S84 or the step S88, the process shown in FIG. 14 will be executed. Since the steps S71 through S77 shown in FIG. 14 are identical to the steps S35 through S41 shown in FIG. 11, the descriptions are omitted. When executing the process shown in FIG. 14 following the step S84 shown in FIG. 17, it advances to step S81 of FIG. 17 if it is judged Yes (affirmative) in the step S76 of FIG. 14; when executing the process shown in FIG. 14 following the step S88 shown in FIG. 17, it advances to step S85 of FIG. 17 if it is judged Yes (affirmative) in the step S76 of FIG. 14. During the laser emission, the sequences shown in the flowchart of FIG. 17 and FIG. 14 are repeated.

As can be seen from the above, the third embodiment not only provides the same effect as in the first embodiment, but also makes it possible to detect the operating condition of the laser emission part 122 for each stroke without having to add a new sensor, but simply adjusting the location of the reciprocating motion detection sensor 166, even in a case when different moving speeds are set for the forward stroke and the backward stroke of the reciprocating motion. Moreover, it makes it possible to detect whether the operation of the laser emission part 122 is proper more quickly.

Figure 18:
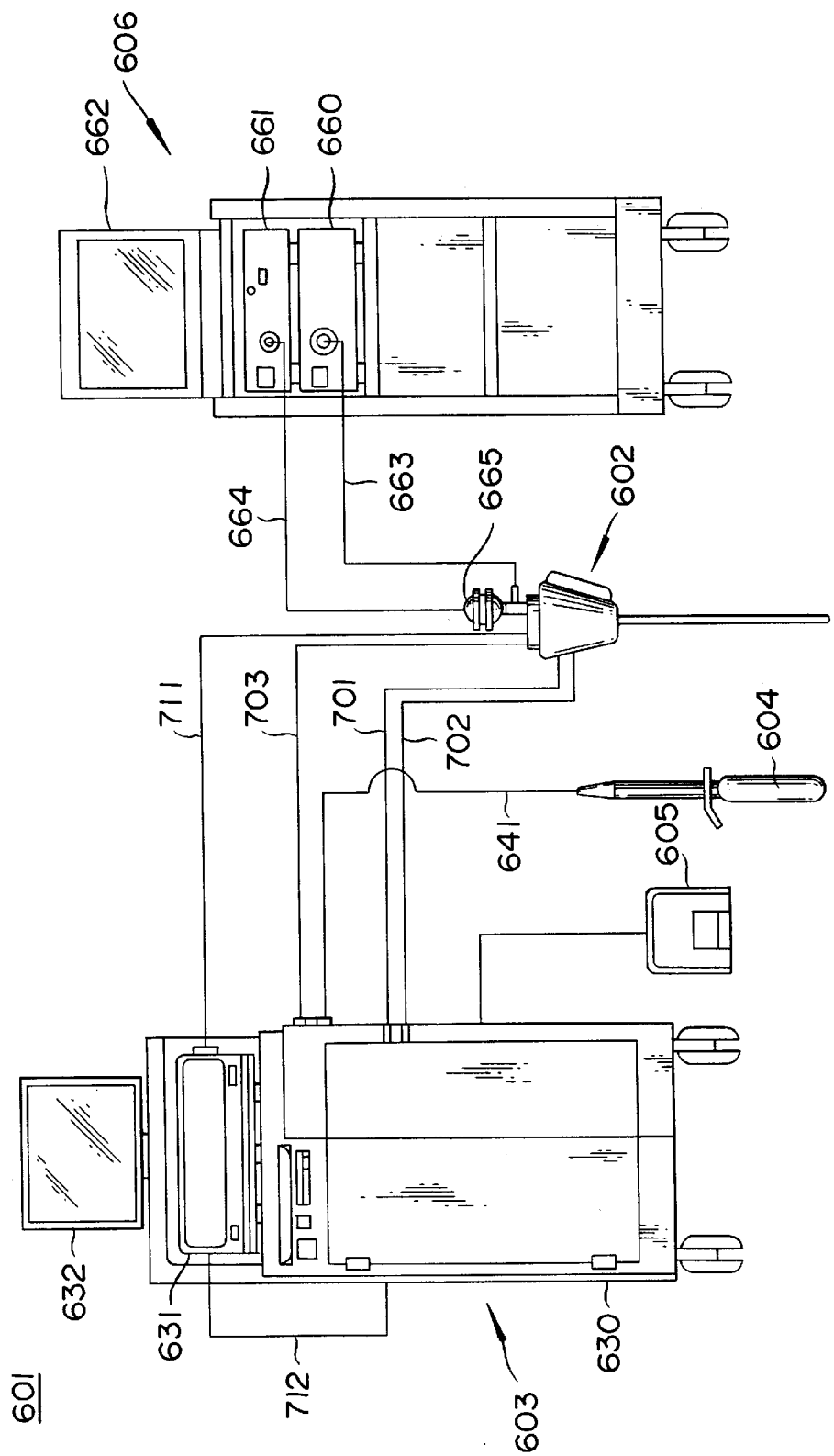
FIG. 18 is a system diagram showing the constitution of a thermal treatment apparatus according to a fourth embodiment.

[Embodiment 4] FIG. 18 is a system diagram showing the constitution of a thermal treatment apparatus according to a fourth embodiment.

A thermal treatment apparatus 601 is for treating benign prostatic hyperplasia or various tumors such as cancer by inserting a urethra applicator 602 into the human body and irradiating tissues with laser beams as energy As shown in FIG. 18, the thermal treatment apparatus 601 includes a urethra applicator 602, a control device 603, a rectum probe 604, a foot switch 605, and an observation unit 606. The urethra applicator 602, the rectum probe 604, and the foot switch 605 are all connected to the control device 603. The urethra applicator 602 is connected to the observation unit 606 as well.

Constitutions of various parts of the thermal treatment apparatus 601 will be described bellow.

The urethra applicator 602 is inserted into a body cavity such as the urethra to irradiate tissue with laser beams. The laser beams are transmitted from a laser generator 631 of the control device 603 via an optical fiber 711 to the urethra applicator 602.

A coolant circulation passage is formed in the inside of the urethra applicator 602 and a coolant passes through this circulation passage to cool the urethra applicator 602 and the surface of the urethra, which is in contact with the urethra applicator 602. The coolant is supplied to the urethra applicator 602 via a water supply tube 701 from the coolant circulation unit installed inside a main controller 630 of the control device 603, and circulated back to the coolant circulation unit via a drain tube 702.

Moreover, a temperature sensor 620 (see FIG. 19) is provided inside the urethra applicator 602 for measuring the temperature of the urethra. The measured temperature of the urethra is transmitted via sensor signal lead wires 703 to the main controller 630 of the control device 603.

The control device 603 consists of the main controller 630, a laser generator 631 and a display/operation unit 632.

The main controller 630 controls the entire operations of the thermal treatment apparatus 601 using the detection signals obtained by sensors provided at the urethra applicator 602 and the rectum probe 604. The main controller 630 also adjusts the irradiation values and irradiation time of the energy irradiated by the urethra applicator 602 by controlling the laser generator 631.

The laser generator 631 is connected to the main controller 630 via a communication cable 712 and generates laser beams as it is controlled by the main controller 630. The display/operation unit 632 receives specified settings and operations as it displays specified information to the user. The display/operation unit 632 can be a touch screen type device or can use input devices such as a keyboard, a mouse, etc., which are not shown here.

The rectum probe 604 is inserted into the rectum through the anus, detects the temperature of the rectum wall, and send the detected temperature to the main controller 630 via a sensor signal lead 641. The foot switch 605 transmits to the main controller 630 a signal indicating that it has been pressed down by the user. Upon receiving the signal, the main controller 630 judges it as an instruction to start the emission if the laser emission has been stopped, and as an instruction to stop the emission if it happens during the laser emission.

The observation unit 606 is equipped with a light source 660 for supplying an illuminating light for endoscope observation, a TV camera 661 for importing the image observed by the endoscope, and a video receiver 662 for displaying images imported into the TV camera 661.

The light source 660 is connected to the endoscope via a light guide 663. The TV camera 661 is connected to a camera head 665 via a camera signal lead wire 664. And the camera head 665 is connected to the endoscope. This makes it possible to perform thermal treatments while observing the inside of the urethra by means of the endoscope built into the urethra applicator 602.

Next, let us describe the specific constitution of the control device 603, which is the center of the control concerning the present invention.

Figure 19:
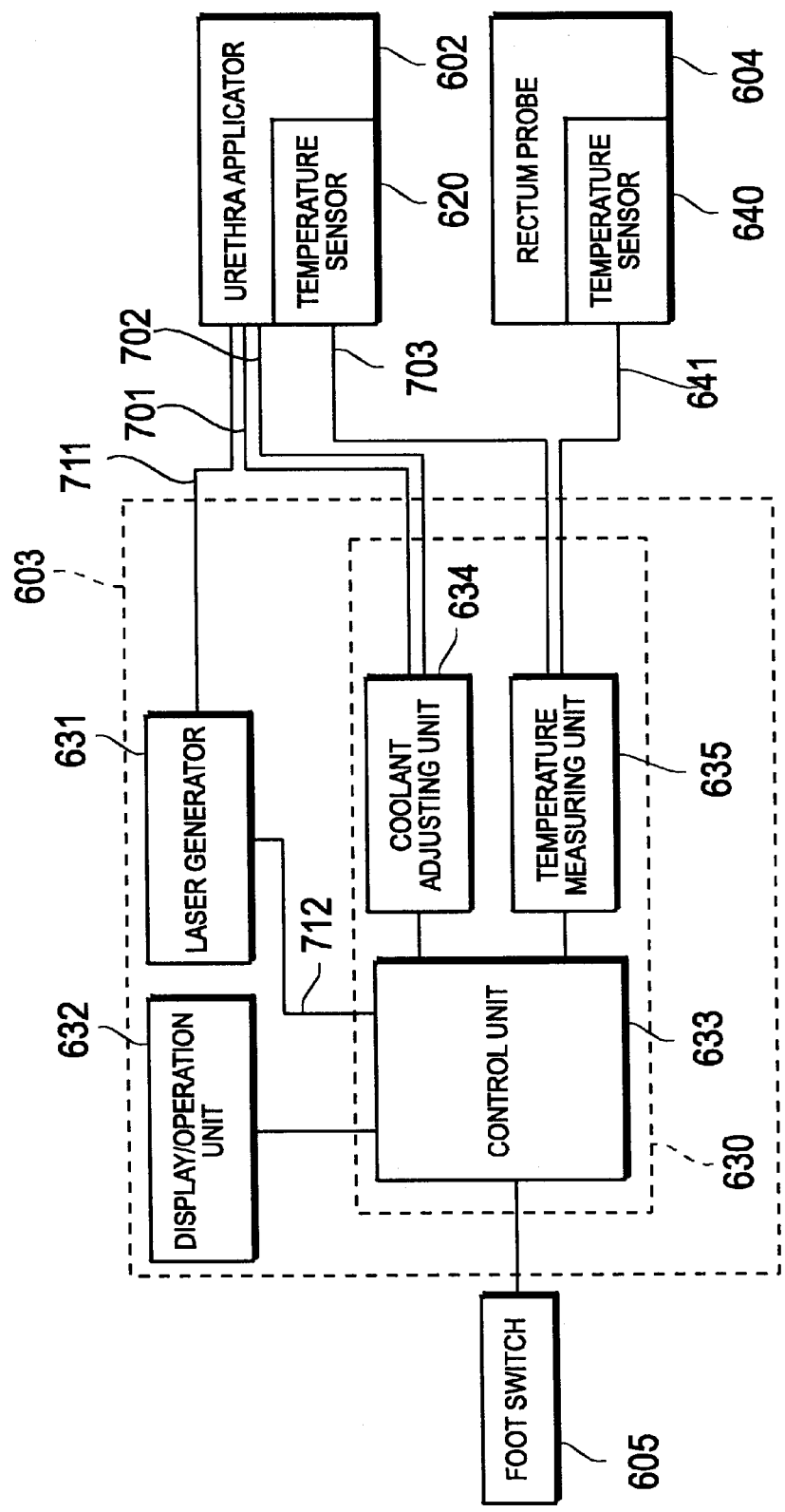
FIG. 19 is a block diagram showing the constitution of the main controller.
Figure 20:
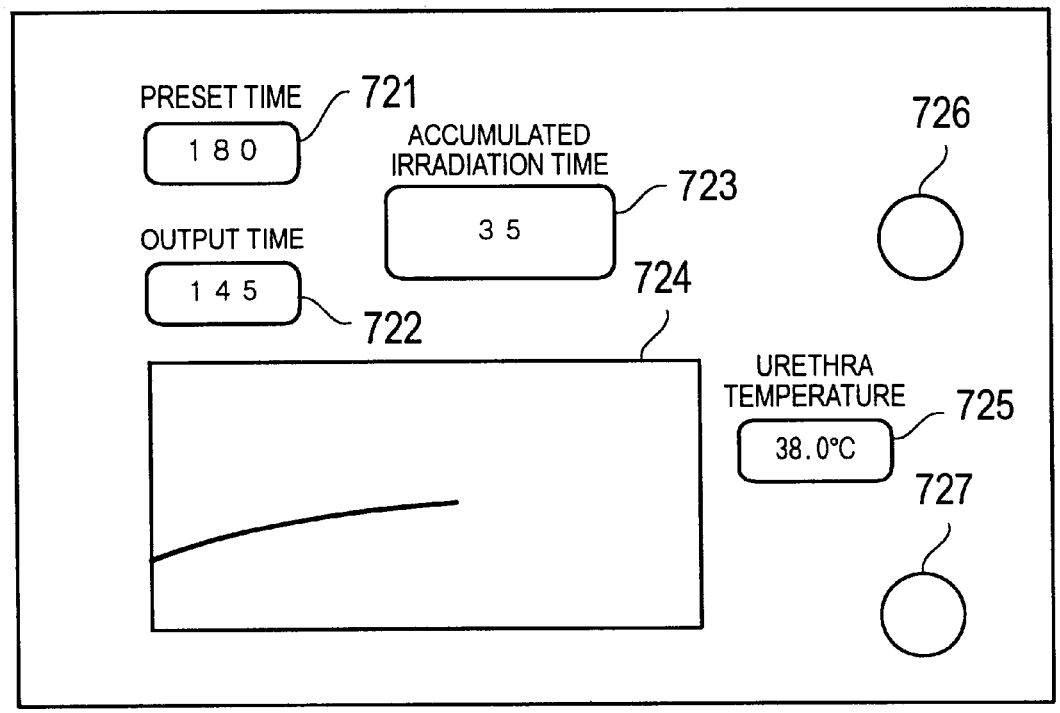
FIG. 20 shows an example display at the display/operation unit.

FIG. 19 is a block diagram showing the constitution of the control device 603. FIG. 20 shows an example display at the display/operation unit 632.

The control device 603 consists of the main controller 630, a laser generator 631 and a display/operation unit 632 as described above with reference to FIG. 18. The main controller 630 further includes a control unit 633, a coolant adjusting unit 634 and a temperature measuring unit 635.

The display/operation unit 632 is used for setting the irradiation value and the irradiation time of the laser beam irradiated by the urethra applicator 602 as described before. The display/operation unit 632 used for such settings has a touch screen as shown in FIG. 20. The user can make various inputs by simply touching the screen, or verify measurements values of various sensors by observing the displayed values.

As shown in FIG. 20, the currently set laser beam irradiation time is indicated in a preset time display part 721 provided on the top left corner of the screen. A remaining irradiation time display part 722 provided below the preset time display part 721 displays the time remaining for laser beam irradiation. When the display on the remaining irradiation time display part 722 becomes "zero," the laser beam irradiation automatically stops.

An accumulated irradiation time display part 723 provided to the right of the preset time display part 721 and the remaining irradiation time display part 722 displays the accumulated time spent for delivering the energy to the tissue. A temperature graph display part 724 provided below the accumulated irradiation time display part 723 displays the chronological change of the urethra temperature measured by the temperature sensor 620. The current urethra temperature is displayed in numerical values in a urethra temperature display part 725 provided on the right side of the temperature graph display part 724.

A finish button 726 provided on the top right corner of the screen is a button for forcibly stopping the laser beam irradiation. The user can instruct the system to stop the laser beam irradiation by touching this stop finish button 726.

A time extension button 727 provided on the bottom right corner of the screen is a button for extending the laser beam irradiation time. The user can instruct the system to extend the laser beam irradiation by touching this time extension button 727.

Let us return to the description of FIG. 19. When the foot switch 605 is pressed down, the control unit 633 controls the laser generator 631 to emit laser beams. The control unit 633 outputs laser beams of the specified value and for the specified time based on the input values set by the user using the display/operation unit 632. The control unit 633 controls the laser generator 631 immediately to stop the irradiation of laser beams when the foot switch 605 is pressed down while the laser generator 631 is irradiating laser beams.

The control unit 633 also monitors the temperature, pressure, flow rate, etc., by means of various sensors (not shown), and controls the coolant adjustment unit 634 so that the coolant is operated at the specified temperature, pressure and flow rate.

Moreover, the system can be arranged is such a way that the control unit 633 controls the coolant adjusting unit 634 based on the signals from the temperature measuring unit 635 that monitors the urethra temperature measured by the temperature sensor 620 provided on the urethra applicator 602, and the rectum temperature measured by the temperature sensor 640 provided on the rectum probe 604.

Consequently, the coolant adjusting unit 634 adjusts the temperature and the flow rate of the coolant to be supplied to the urethra applicator 602 according to the control of the control unit 633. For example, if the temperatures measured by the temperature sensor 620 and the temperature sensor 640 become higher than the specified values, the control unit 633 judges that the urethra and the rectum have abnormally heated. Based on this judgment, the coolant adjustment unit 634 increases the flow rate of the coolant or lower the temperature of the coolant supplied to the urethra applicator 602. On the contrary, if the temperature of the urethra becomes lower than the specified value, the coolant adjusting unit 634 can decrease the flow rate of the coolant supplied to the urethra applicator 602, or increase the temperature of the coolant.

The temperature measuring unit 635 combines the temperatures measured by the temperature sensor 620 and the temperature sensor 640 and transmits them to the control unit 633.

The thermal treatment apparatus 601 constituted as described in the above functions as follows.

Figure 21:
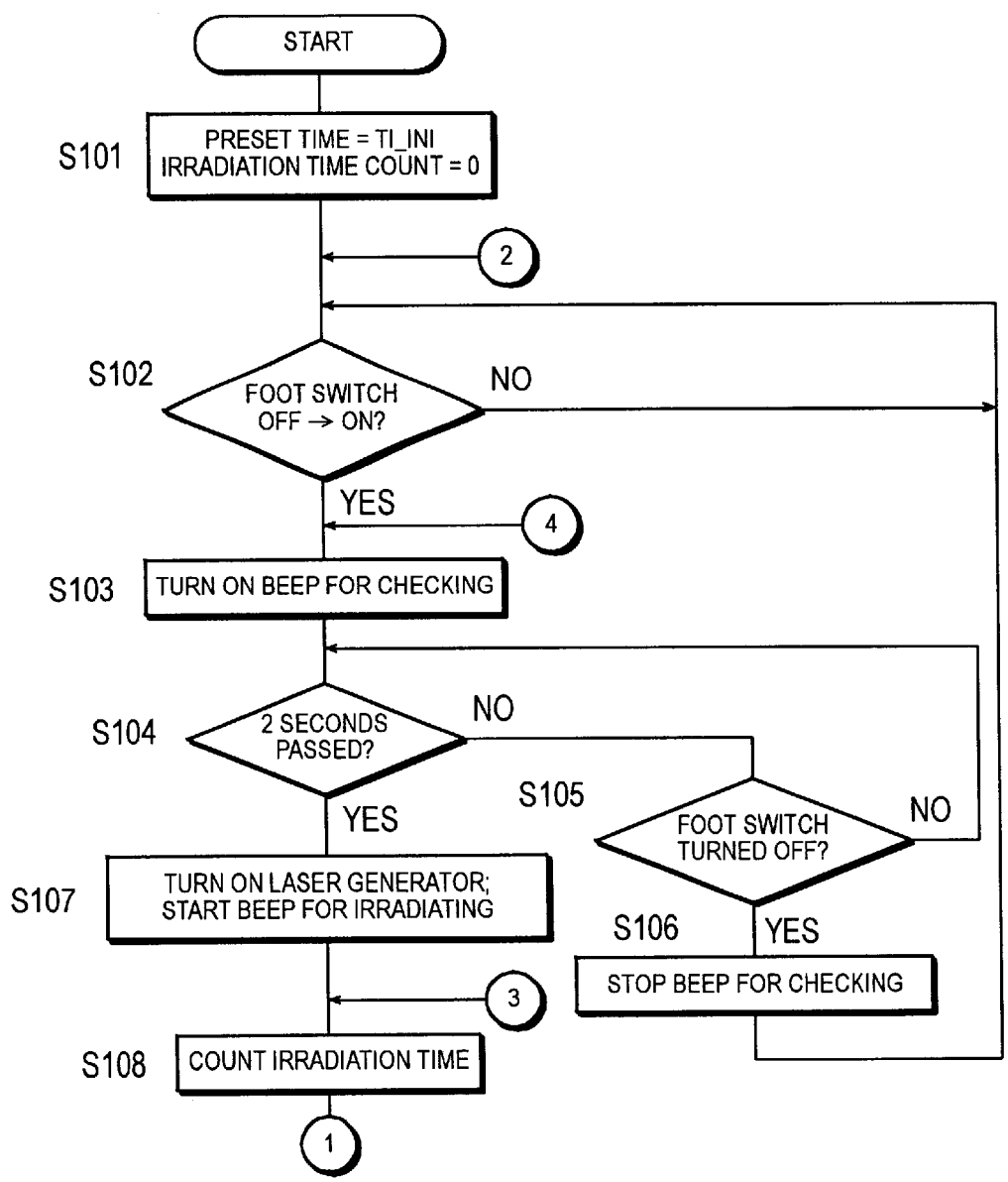
FIG. 21 is a flowchart showing the operation of the thermal treatment apparatus.
Figure 22:
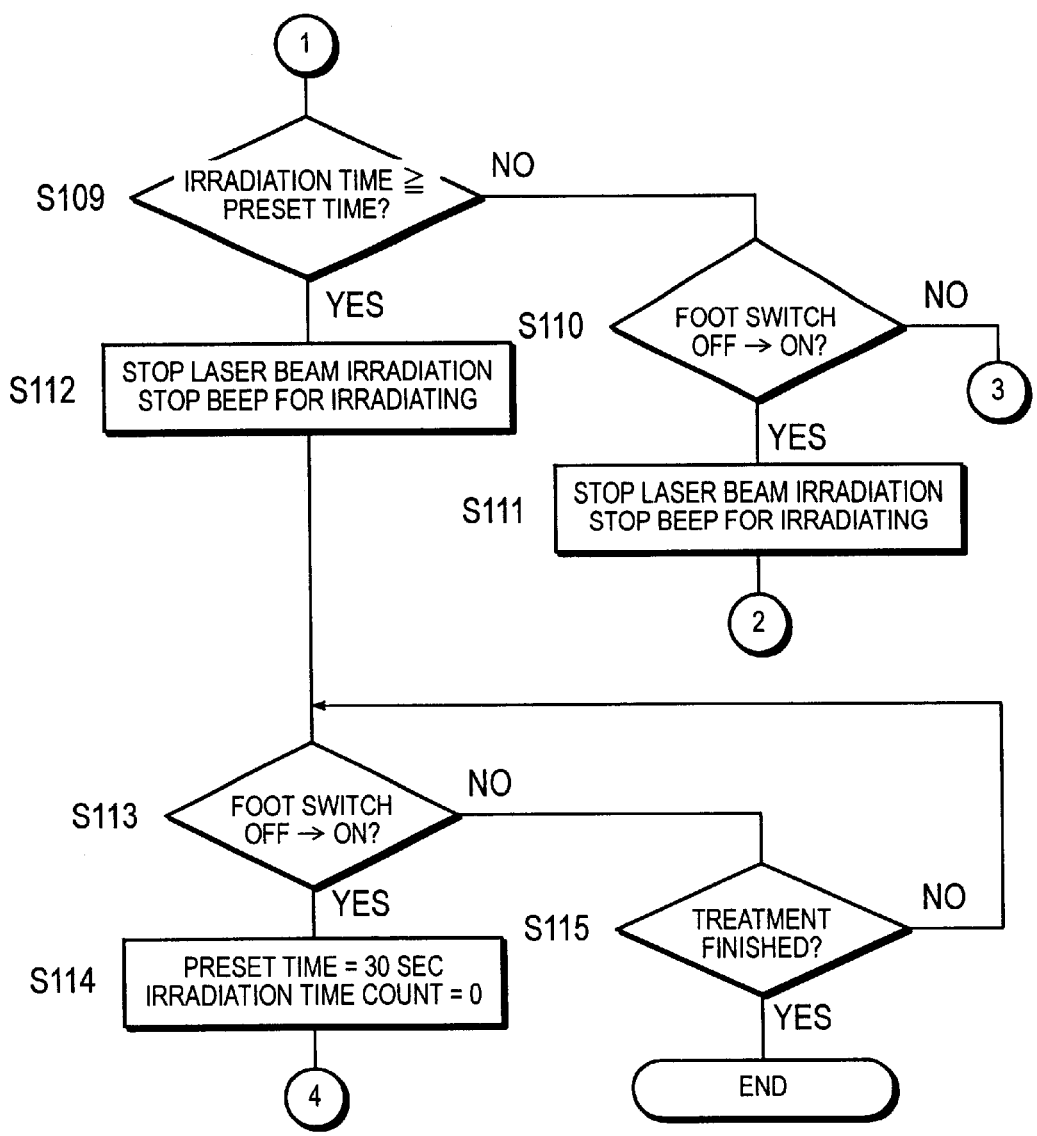
FIG. 22 is a continuation of the flowchart showing the operation of the thermal treatment apparatus shown in FIG. 21.

FIG. 21 is a flowchart showing the operation of the thermal treatment apparatus 601 and FIG. 22 is a continuation of the flowchart showing the operation of the thermal treatment apparatus 601 shown in FIG. 21.

First, a laser beam irradiation time T_ini (sec) is set on the display/operation unit 632 of the thermal treatment apparatus 601 as a preset time according to the treatment plan, and the laser beam irradiation time count is cleared to "zero" (S101). The time period in which the laser beam is being emitted is measured by the control unit 633 of the control device 603, constantly updated, and stored. The initial preset time T_ini should preferably be 180–300 sec.

The control unit 633 makes a judgment as to whether the foot switch 605 is stepped on by the user to be turned on (S102). The control unit 633 waits until it turns on if the foot switch 605 is not turned on (S102: No), and, if it is turned on (S102: Yes), causes the sounding unit provided on the thermal treatment apparatus 601 to issue a beep for checking to remind the user that the foot switch 605 is turned on and the user is turning on the laser beam by pressing down the foot switch 605 (S103).

The control unit 633 makes a judgment as to whether 2 seconds have passed since the foot switch 605 was turned on (S104). If it has not bee 2 seconds (S104: No), the control unit 633 makes a judgment as to whether the foot switch 605 has been turned off (S105). If the foot switch 605 is not turned off (S105: No), in other words, the foot switch 605 is continuously being stepped on as the beep for checking is being issued, the system returns to the process of the step S104. If the foot switch 605 is turned off (S105: Yes), the control unit 633 stops the beep for checking (S106), and returns to the process of the step S102.

On the other hand, if it has been 2 seconds since the foot switch 605 is turned on (S104: Yes), it means that the foot switch 605 has been turned on for 2 seconds, so that the control unit 633 controls the laser generator 631 to activate the laser beam emission, stops the beep for checking, and issues the beep for irradiating anew for reminding that the laser beam will be emitted (S107). Although 2 seconds is set as the confirmation time for confirming the start of laser beam irradiation in the step S104 to make a judgment as to whether 2 seconds have passed since the foot switch 605 is turned on, the invention is not limited to such a timing. This confirmation time can be arbitrarily set up.

As soon as the laser beam is irradiated, the control unit 633 starts counting the laser beam emission time by means of the irradiation time count (S108). Once the laser beam irradiation is started, the laser beam will be continued to be irradiated until the preset time is completed even if the user stops to press down the foot switch 605 and the foot switch 605 is turned off. Thereafter, each time when the foot switch 605 is turned from Off to On, in other words, turning the foot switch 605 on, then off for a while, and on again, the laser irradiation is turned on and off.

The control unit 633 makes a judgment as to whether the irradiation time count is greater than the preset time (S109). If the irradiation time count is smaller than the preset time (S109: No), the control unit 633 makes a judgment whether the foot switch 605 is turned on again after it is turned off since the laser beam emission has started (S110).

If the foot switch 605 is not switched from Off to On (S110: No), the control unit 633 repeats the process starting from the step S108 of FIG. 21. If the foot switch 605 is switched from Off to On (S110: Yes), the control unit 633 judges that the user instructed to stop the laser beam emission, stops the laser emission, and stops the beep for irradiating as well (S111) to return to the process of the step S102.

On the other hand, if the irradiation time count is greater than the preset time (S109: Yes), it means that the irradiation of the laser beam for the preset time is completed, so that the control unit 633 stops the irradiation of the laser beam and the beep for irradiating (S112).

Next, the control unit 633 makes a judgment as to whether the foot switch 605 is switched from Off to On (S113). If the foot switch 605 is switched from Off to On (S113: Yes), the control unit 633 resets the preset time to 30 seconds and the irradiation time count to zero (S114), and returns to the process of the step S103. Here, the preset time for the second preset time cycle and thereafter is chosen to be a shorter one than the initial preset time T_ini.

If the foot switch 605 is not switched from Off to On (S113: No), the control unit 633 makes a judgment as to whether the display/operation unit 632 has indicated the completion of the treatment (S115). If the treatment completion is not indicated (S115: No), the control unit 633 repeats the processes starting from the step S113. If the treatment completion is indicated (S115: Yes), the thermal treatment apparatus 601 terminates the thermal treatment.

In the above description, the laser beam irradiation start or stop is switched when the foot switch 605 is switched from the Off state (not pressed down state) to the On state (pressed down state). However, the laser beam irradiation start or stop is not switched if the foot switch 605 is continuously in the On state (pressed down state).

Here, although the preset time for the second preset time cycle and thereafter is chosen to be a shorter one than the initial preset time T_ini, the invention is not limited to it. The preset time for the second preset time cycle or thereafter can be set up as a significant function of the first preset time.

As can be seen from the above, the thermal treatment apparatus 601 of the present embodiment allows the user to add the laser beam irradiation time as the preset time can be updated to start the laser beam irradiation by simply turning on the foot switch 605 again after the preset time has passed, thus allowing the user to add the laser beam irradiation time based on an instantaneous decision. Moreover, since the laser beam irradiation time can be easily done, it is possible to add the irradiation time to continue the thermal treatment before the tissue temperature, which has been raised by laser beam irradiation, drops down, thus contributing to achieving a stable treatment effect.

In addition, the thermal treatment apparatus 601 of the present embodiment presets the confirmation time for confirming the start of the output before starting the laser beam irradiation, so that, even when the foot switch 605 is turned on by mistake, the laser beam irradiation does not occur if the foot switch 605 is turned off immediately, thus preventing any misapplication of laser beams.

Further, in the thermal treatment apparatus 601 of the present embodiment, the laser beam irradiation continues without interruption once the irradiation is activated and the laser beam irradiation stops automatically when the preset time is reached, so that the user's operational burden can be reduced.

Furthermore, in the thermal treatment apparatus 601 of the present embodiment, the irradiation time count does not get reset regardless of how many times starts and stops occur until the preset time is reached once the laser beam irradiation starts. Consequently, the laser beam irradiation can be run until the preset time is reached without resetting the irradiation time when restarting the irradiation after the laser beam irradiation has stopped.

It is also possible to combine the constitution and control method for facilitating additional irradiations to be performed after the preset amount of laser beam irradiation as shown in the fourth embodiment (as well as a fifth through seventh embodiments described below) with the constitutions and control methods for securing preferable reciprocating and stopping motions of the laser emission part as shown in the first through third embodiments

[Embodiment 5] A fifth embodiment provides a means of setting up an upper limit to the number of preset time output cycles to be added after the laser beam irradiation of the preset time is completed in addition to the features provided by the fourth embodiment.

The thermal treatment apparatus 601 of the fifth embodiment has the identical constitution as that of the fourth embodiment shown in FIG. 18 through FIG. 20. Therefore, the description of the thermal treatment apparatus 601 will be omitted here and only its operation will be described.

Figure 23:
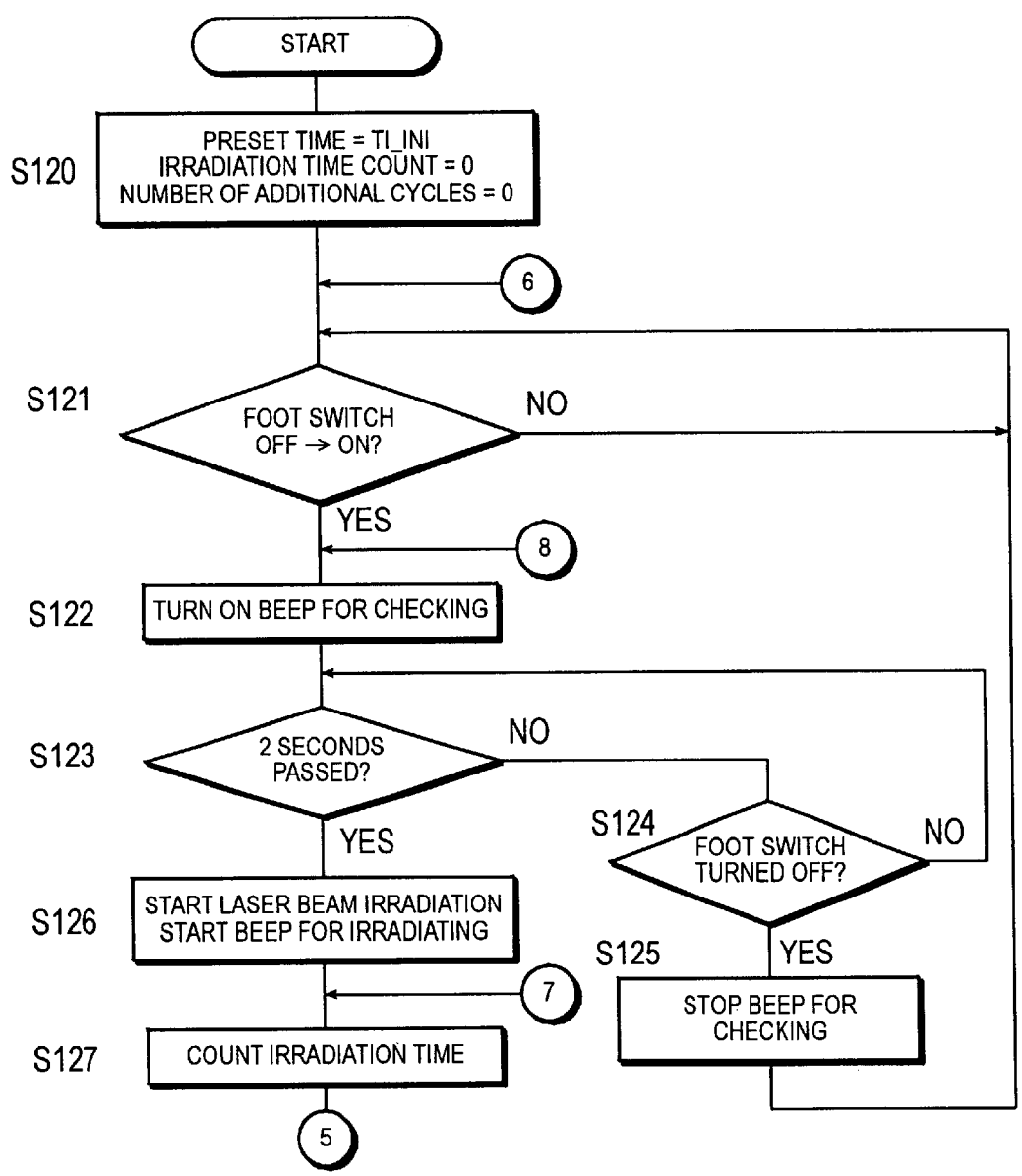
FIG. 23 is a flowchart showing the operation of the thermal treatment apparatus.
Figure 24:
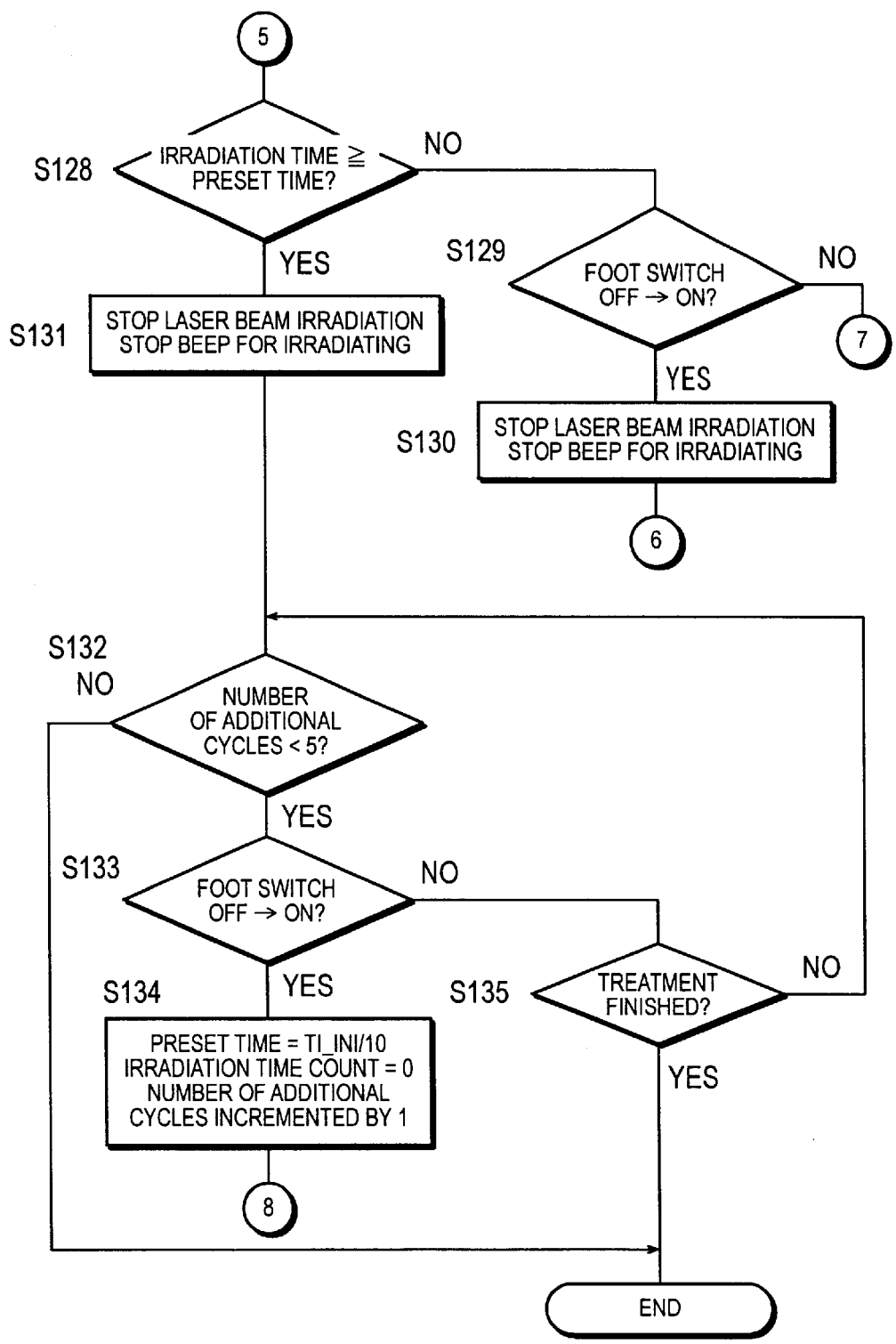
FIG. 24 is a continuation of the flowchart showing the operation of the thermal treatment apparatus shown in FIG. 23.

FIG. 23 is a flowchart showing the operation of the thermal treatment apparatus. FIG. 24 is a continuation of the flowchart showing the operation of the thermal treatment apparatus shown in FIG. 23.

The processes in the steps S121 through S127 in FIG. 23 are identical to those of the steps S102 through S108 in FIG. 21, so that their descriptions shall be omitted. The processes in the steps S128 through S130 in FIG. 24 are also identical to those of the steps S109 through S111 in FIG. 22, so that their descriptions shall be omitted.

First, a laser beam irradiation time T_ini (sec) is set on the display/operation unit 632 of the thermal treatment apparatus 601 as a preset time according to the treatment plan, the laser beam irradiation time count is cleared to "zero," and further the initial number of additional cycles is set to "zero" (S120).

The number of additional cycles means the number of laser beam irradiation cycles to be added after the laser beam irradiation is completed by reaching the initial preset time is reached. The time period in which the laser beam is being emitted is measured by the control unit 633 of the control device 603, constantly updated, and stored. The initial setting time T_ini should preferably be 180–300 sec.

The thermal treatment apparatus 601 performs the processes of the steps S122 through S131. When the irradiation time exceeds the preset time, i.e., the laser beam irradiation has passed the preset time (S128: Yes), the system stops the laser beam irradiation and the beep for irradiating (S131).

Next, the control unit 633 makes a judgment as to whether the number of the added preset time cycles is less or, equal or more, than five times based on the number of additional cycles is less than five (S132). If the number of additional cycles is equal or more than five, in other words, the number of the added preset time cycles is not less than five (S132: No), the control unit 633 judges that further addition of preset time should not be allowed, and the thermal treatment apparatus 601 terminates the thermal treatment.

Further, if the number of additional cycles is less than five, in other words, the number of the added preset time cycles is less than five (S132: Yes), the control unit 633 makes a judgment as to whether the foot switch 605 is switched from Off to On (S133).

If the foot switch 605 is switched from Off to On (S133: Yes), the control unit 633 resets the preset time to T_ini/10 (seconds), resets the irradiation time count to zero, and increments the number of additional cycles by one (S134), and returns to the process of the step S122. Here, the preset time for the second preset time cycle and thereafter is determined as a function of the initial preset time T_ini, i.e., to be 1/10 of the initial preset time T_ini.

When the foot switch 605 is not switched from Off to On (S133: No), the control unit 633 makes a judgment whether the user instructed the completion of the treatment from the display/operation unit 632 (S135). If the treatment completion is not indicated (S135: No), the control unit 633 repeats the processes starting from the step S132. If the treatment completion is indicated (S135: Yes), the thermal treatment apparatus 601 terminates the thermal treatment.

Although the preset time for the second preset time cycle and thereafter is determined as a function of the initial preset time T_min in the step S134, the invention is not limited to it. The preset time for the second preset time cycle and thereafter can be a predetermined time (e.g., 30 seconds).

Furthermore, it is also possible not to define the upper limit for the number of times the preset time can be added but rather to define the preset time for the second preset time cycle and thereafter as 1/n (n>1) times of the initial preset time.

As can be seen from the above, the fifth embodiment provides an effect in addition to those of the fourth embodiment that it can prevent unusually long period of laser beam irradiation after the initial preset time has passed as the upper limit for the number of times preset time can be added, i.e., the number of laser beam irradiation cycles that can be added, is set.

Furthermore, in the fifth embodiment, it is possible to add a significant preset time to the initial preset time as the preset time for the second preset time cycle and thereafter is weighted relative to the initial preset time. For example, if the preset time for the second preset time cycle and thereafter be $1/10$ of the initial preset time and the number of additional cycles is five, the total time that can be added to the period of laser beam irradiation is up to 50% of the initial preset time, so that any unintended time extension can be avoided.

[Embodiment 6] A sixth embodiment provides a means of extending the preset time during the laser beam emission by pressing a time extension button 727 of the display/operation unit 632 in addition to the features provided by the fourth and fifth embodiments.

The thermal treatment apparatus 601 of the sixth embodiment has the identical constitution as that of the fourth embodiment shown in FIG. 18 through FIG. 20. Therefore, the description of the thermal treatment apparatus 601 in the sixth embodiment will be omitted here and only its operation will be described. Since the operations of the thermal treatment apparatus 601 are identical to those shown in FIG. 23, only those operations that follow the operations of FIG. 23 will be described referring to FIG. 25.

Figure 25:
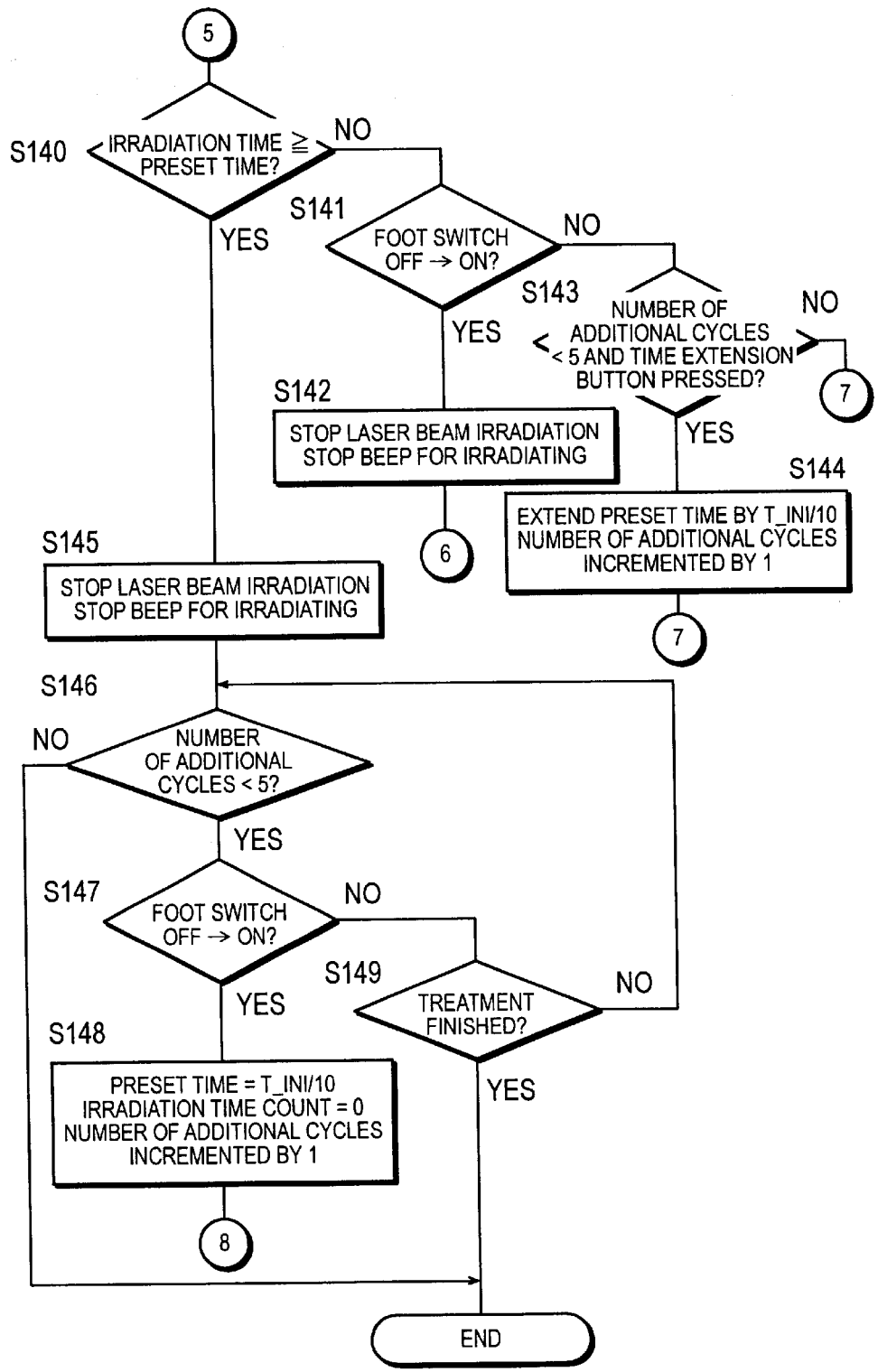
FIG. 25 is another continuation of the flowchart showing operations of the thermal treatment apparatus shown in FIG. 23.

FIG. 25 is a continuation of the flowchart showing other operations of the thermal treatment apparatus shown in FIG. 23.

In the process shown in FIG. 23, the thermal treatment apparatus 601 starts the irradiation of the laser beam for the preset time.

The control unit 633 makes a judgment as to whether the laser beam irradiation time count is greater than the setup time (S140).

If the irradiation time is not greater than the preset time (S140: No), the control unit 633 makes a judgment whether the foot switch 605 is turned on during the laser beam emission (S141). If the foot switch 605 is turned on (S141: Yes), the control unit 633 stops the laser beam irradiation, stops the beep for irradiating (S142), and returns to the step S121 of FIG. 23.

If the foot switch 605 is not turned on during the laser beam irradiation (S141: No), the control unit 633 makes a judgment as to whether the number of additional cycles is less than five, and the time extension button 727 is pressed (S143). If the number of additional cycles is less than five and the time extension button 722 has been pressed down (S143: Yes), the control unit 633 increases the current preset time by $1/10$ of the initial preset time T_ini, and increment the number of additional cycles by one (S144). The control unit 633 then returns to the step S127 of FIG. 23.

If the number of additional cycles is less than five and the time extension button 722 has not been pressed down (S143: No), the control unit 633 simply returns to the step S127 of FIG. 23.

On the other hand, if the irradiation time is greater than the preset time (S140: Yes), the control unit 633 advances to the process of the step S145. The processes in the steps S145 through S149 in FIG. 25 are identical to those of the steps S131 through S135 in FIG. 24, so that their descriptions shall be omitted.

In the above descriptions, the pressing down of the time extension button 727 means touching the display of the time extension button 727 if the display/operation unit 632 is a touch screen.

Moreover, although it was described that the preset time is increased $1/10$ of the initial preset time T_ini in the above in increasing the reset time in the step S144 and the step S148, the invention is not limited to it. The preset time can be increased for a predetermined time, e.g., 30 seconds.

Furthermore, although the upper limit of the number of additional cycles is set in the sixth embodiment as in the fifth embodiment, it does not have to be set either.

As can be seen above, the sixth embodiment provides a means of easily extending the irradiation time before the laser beam irradiation stops by pressing down the time extension button 727 during the laser beam irradiation in addition to the features provided by the fourth and fifth embodiment.

[Embodiment 7] A seventh embodiment provides in addition to the features provided by the fourth and fifth embodiments a means of stopping the laser beam irradiation if the temperature of urethra detected by the temperature sensor 620 provided on the urethra applicator 602 becomes higher than the preset temperature during the laser beam irradiation of the preset time of the second preset time cycle and thereafter.

The thermal treatment apparatus 601 of the seventh embodiment has the identical constitution as that of the fourth embodiment shown in FIG. 18 through FIG. 20. Therefore, the description of the thermal treatment 601 will be omitted.

Figure 26:
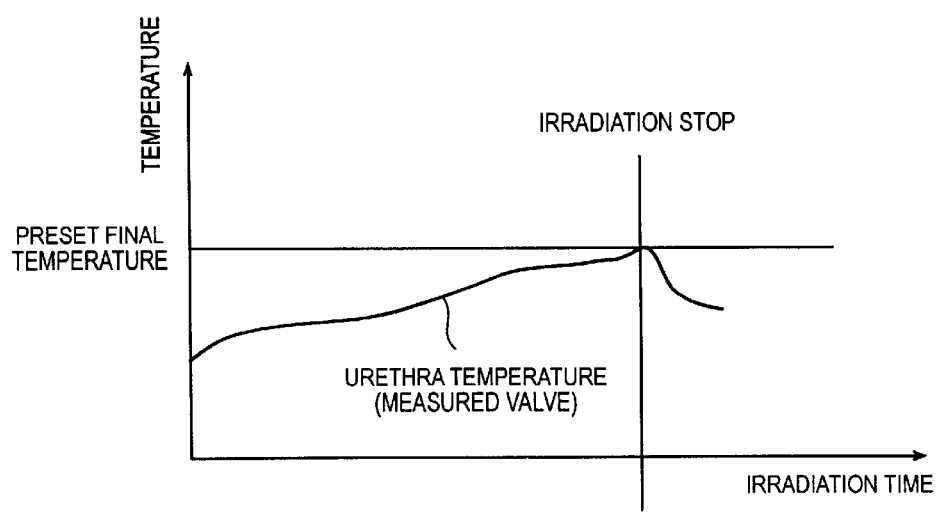
FIG. 26 is a temperature graph displayed on the display unit.

The thermal treatment apparatus 601 of the seventh embodiment detects the temperature of the urethra by means of the temperature sensor 620 provided on the urethra applicator 602. The measured temperature is displayed on the temperature graph display part 724 of the display/operation unit 632 as shown in FIG. 20. FIG. 26 is an enlarged view of the temperature graph display unit 724.

The user can set up the temperature of the urethra, which is going to be used as the condition of stopping the laser beam irradiation, on the display/operation unit 632, while observing the temperature graph display part 724. The temperature of the urethra that is used as the condition for stopping the laser beam irradiation will be hereinafter called the preset final temperature. When the temperature of the urethra reaches the preset final temperature and the laser beam irradiation is stopped, the temperature of the urethra will no longer increase as shown in FIG. 26.

Next, the operations of the thermal treatment apparatus 601 of the seventh embodiment will be described. Since the operations of the thermal treatment apparatus 601 in the seventh embodiment are identical to those shown in FIG. 23, only those operations that follow the operations of FIG. 23 will be described referring to FIG. 27.

Figure 27:
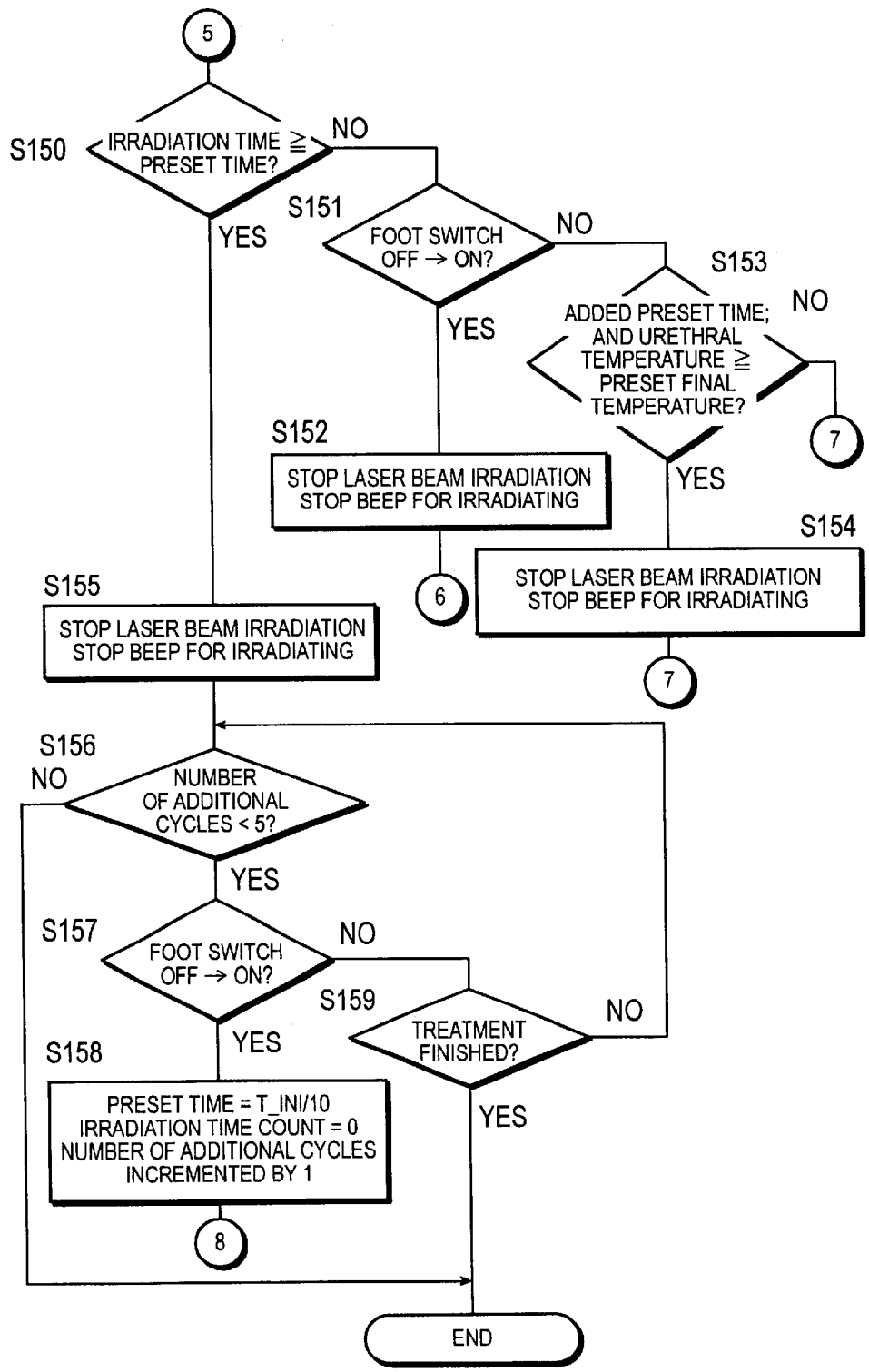
FIG. 27 is yet another continuation of the flowchart showing the operation of the thermal treatment apparatus shown in FIG. 23.

FIG. 27 is a continuation of the flowchart showing the operation of the thermal treatment apparatus shown in FIG. 23.

In the process shown in FIG. 23, the thermal treatment apparatus 601 starts the irradiation of the laser beam for the preset time.

The control unit 633 makes a judgment as to whether the laser beam irradiation time count is greater than the setup time (S150).

If the irradiation time is not greater than the preset time (S150: No), the control unit 633 makes a judgment whether the foot switch 605 is turned on during the laser beam emission (S151). If the foot switch 605 is turned on (S151: Yes), the control unit 633 stops the laser beam irradiation, stops the beep for irradiating (S152), and returns to the step S121 of FIG. 23.

If the foot switch 605 is not turned on during the laser beam irradiation (S151: No), the control unit 633 makes a judgment as to whether it is the laser beam emission during the added preset time, i.e., the laser beam during the preset time of the second preset time cycle and thereafter, and the temperature of the urethra is higher than the preset final temperature (S153).

If it is the laser beam emission during the added preset time, and the urethra temperature is higher than the preset final temperature (S153: Yes), the control unit 633 stops the laser beam irradiation and the beep for irradiating (S154). Then the thermal treatment 601 terminates the thermal treatment.

If it is the laser beam emission during the added preset time, and the urethra temperature is not higher than the preset final temperature (S153: No), the control unit 633 returns to the process of the step S127 of FIG. 23.

On the other hand, if the irradiation time is greater than the preset time (S150: Yes), the control unit 633 advances to the process of the step S155. The processes in the steps S155 through S159 in FIG. 27 are identical to those of the steps S131 through S135 of FIG. 24, so that their descriptions shall be omitted.

As can be seen from the above, the seventh embodiment provides a means of preventing excessively high urethra temperatures affecting the tissue by stopping the laser beam irradiation when the urethra temperature gets higher than the preset final temperature during the laser beam irradiation during the second preset time cycle and thereafter, thus further stabilizing the treatment effect.

Figure 28:
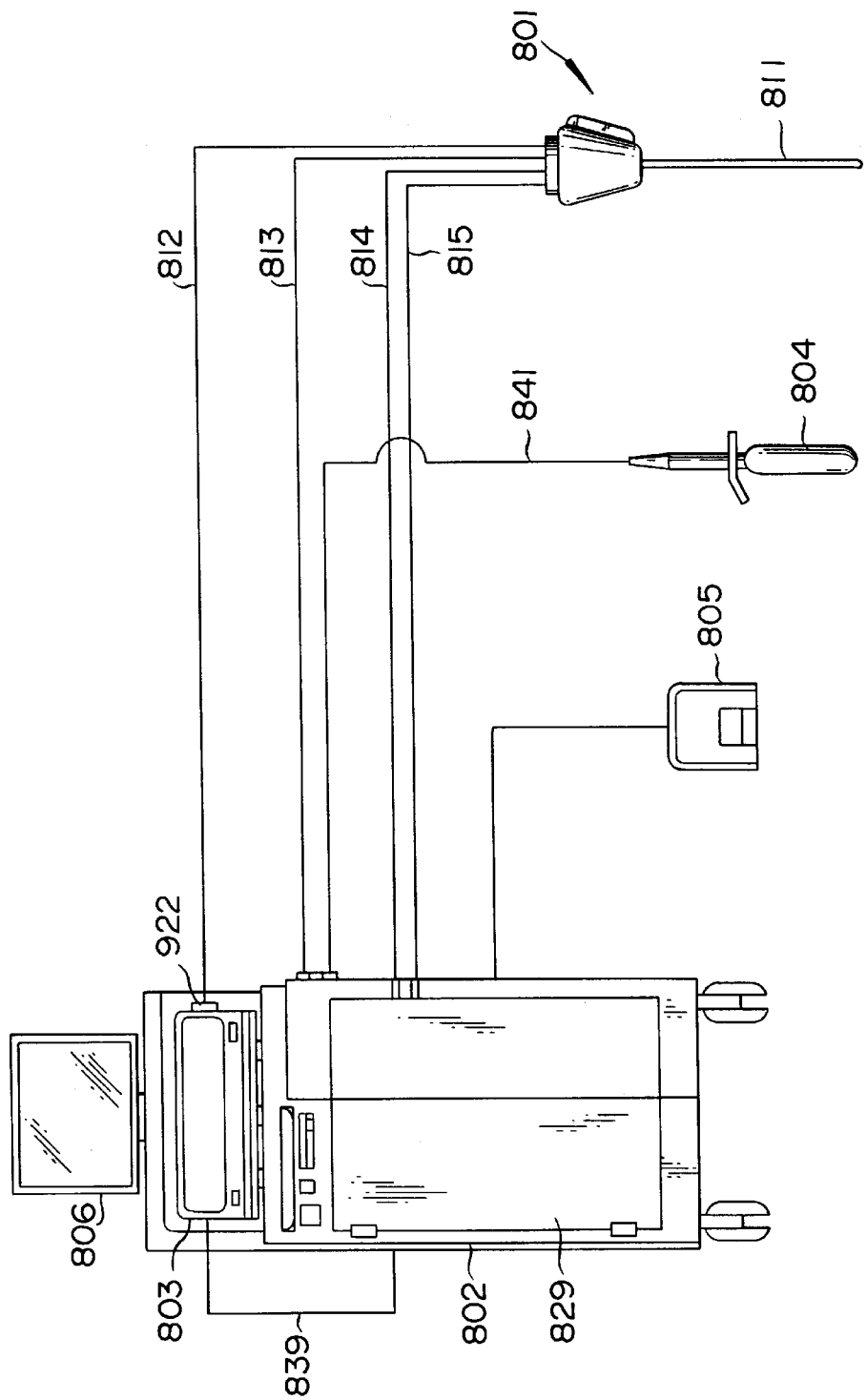
FIG. 28 is a system diagram showing the constitution of a thermal treatment apparatus according to an eighth embodiment.

[Embodiment 8] FIG. 28 is a system diagram showing the constitution of a thermal treatment apparatus according to an eighth embodiment.

The thermal treatment apparatus is intended for treating benign prostatic hyperplasia and tumors such as cancer by irradiating affected tissues with laser beams from a laser irradiation unit 801 inserted into the human body as an energy irradiation unit.

As shown in FIG. 28, the thermal treatment apparatus is equipped with the laser irradiation unit 801, a main controller 802, a laser generator 803 as an energy supply device, a rectum probe 804, a foot switch 805, and a display/operation unit 806. The laser irradiation unit 801, the laser generator 803, the rectum probe 804, the foot switch 805, and the display/operation unit 806 are all connected to the main controller 802.

Their constitutions will be described briefly in the following.

The laser irradiation unit 801 is inserted into a body cavity such as the urethra to irradiate tissue with laser beams. The main controller 802 controls the motions of the entire thermal treatment apparatus using various detection sensors provided on the laser irradiation unit 801 and the rectum probe 804. The main controller 802 controls the laser generator 803 to cause the laser irradiation unit 801 to irradiation a desired energy.

The laser generator 803 is connected to the main controller 802 via a communication cable 839 and generates laser beams based on information received from the main controller 802.

The rectum probe 804 is inserted into the rectum through the anus, detects the temperature of the rectum wall where the prostate is located, and send the detected temperature to the main controller 802 via a sensor signal lead 841. The foot switch 805 outputs a signal to prompt the control device 802 to start laser beam irradiation when the operator steps it on.

The display/operation unit 806 receives specified settings and operations as it displays specified information to the user. The display/operation unit 806 can be a touch screen type device or can use input devices such as a keyboard, a mouse, etc., which are not shown here.

Next, the constitution concerning the present information will be described specifically.

Figure 29:
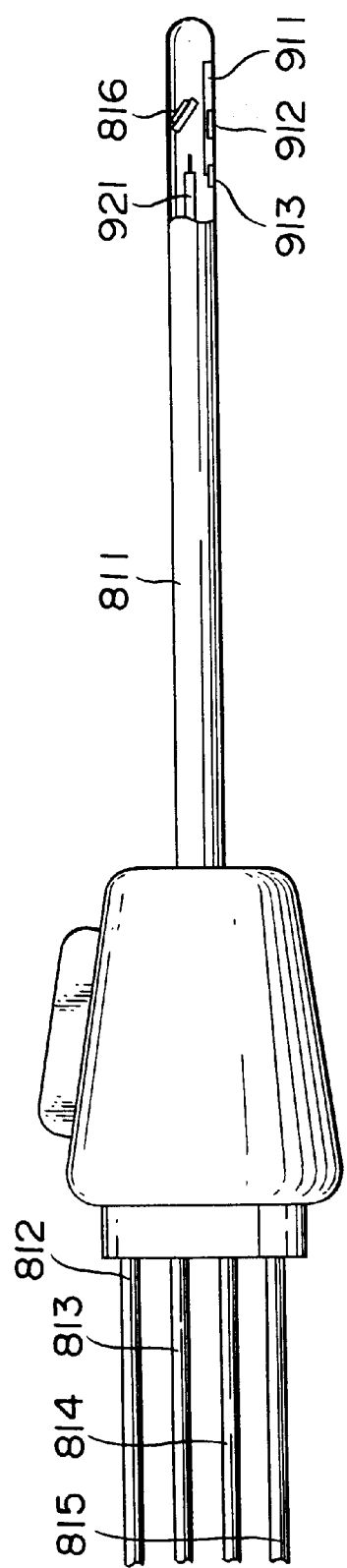
FIG. 29 is an enlarged view of the laser irradiation unit.

First, the laser irradiation unit 801 will be described referring to FIG. 28 and FIG. 29. FIG. 29 is an enlarged view of the laser beam irradiation unit 801.

The laser irradiation unit 801 is equipped with a urethra insertion unit 811, a laser transmission unit 812, a laser signal cable 813, a water supply tube 814, and a drain tube 815. The laser transmission unit 812, the urethra signal cable 813, the water supply tube 814, and the drain tube 815 are all extending from the laser irradiating unit 801.

The urethra insertion unit 811 is formed in a long and slender shape, is inserted into the urethra, and irradiates laser beams to tissues. The laser transmission unit 812 is made of an energy transmitting member such as an optical fiber, and is connected to the laser generator 803 via an optical fiber connector 922. The laser transmission unit 812 transmits the laser beam generated by the laser generator 803 to the urethra insertion unit 811.

As can be seen from FIG. 29, the laser beam that has been transmitted through the laser transmission unit 812 is led to the distal part 921 of the urethra insertion unit 811, is irradiated toward a flat laser reflection surface 816 that reflects laser beams, and is reflected. The urethra insertion unit 811 has a window 911 opening on the side surface in the vicinity of the distal part, and is covered by a laser transmitting covering material (not shown). The laser beam reflected by the laser reflection surface 816 is irradiated sideway through the window 911. The laser reflection surface 816 is located on the position facing forward of the distal part 921, and is capable of irradiating with a concentration on a particular area of the tissue while reciprocating along the lengthwise direction of the urethra insertion unit 811.

The urethra signal cable 813 transmits information detected by two temperature sensors 912 and 913 provided on the window 911 to the main controller 802. The temperature sensor 912 is located at a position where it is not irradiated by laser beams and the temperature sensor 913 is located at a position where it is partially irradiated by laser beams.

The water supply tube 814 and the water drain tube 815 are connected to a coolant circulation unit (not shown) located inside behind the cooling unit door 829 of the main controller 802. The coolant contained in the coolant circulation unit is led to the laser irradiation unit 801 via the water supply tube 814 and returned to the coolant circulation unit via the drain tube 815. The coolant led to the laser irradiation unit 801 passes through the circulating passage formed inside the urethra insertion unit 811, cools the laser reflection surface 816, and cools the tissue via the window 911 of the urethra insertion unit 811.

The laser irradiation unit 801 described above has a shorter longevity than the energy supply unit, and is discarded or replaced after being used only once or several times. The laser irradiation unit 801 is replaced together with components ranging from the optical fiber connector 922 through the urethra insertion unit 811 when it is replaced. Therefore, the transmission efficiency of the laser beam can vary each time due to the replacement of the optical fiber as well as the replacement of the optical fiber connector 922 and the laser generator 803.

The laser irradiation unit 801 according to the present invention is measured of its laser beam transmission efficiency during its production stage and is given a product identification number that contains the measured transmission efficiency. The product identification number is directly indicated on the wrapping (not shown) of the laser irradiation unit 801 or a part of the laser irradiation unit 801.

This product identification code consists of the product's identification information, the laser beam transmission efficiency information, and the checksum integrally codified. More specifically, if the manufacturing number of a particular product is "012345" and its measured laser beam transmission efficiency is 75%, the product identification code includes "012345" in the upper 6 digits and the following three digits contain the laser beam transmission efficiency "075." Furthermore, the product identification code contains the unit digit of the sum of "012345" plus "075." Since the sum is 0+1+2+3+4+5+0+7+5=27 in this case, the checksum is the unit digit of 27, i.e., 7.

Thus, the product identification code in the above case is a 10 digits number, "0123450757." By including the checksum in the product identification code, an input error in entering the product identification code can be easily detected as it would cause the checksum to be different from the unit digit of the sum of the numbers other than the checksum digit.

The transmission efficiency of the laser beam includes not only the laser beam transmitting factor of the optical fiber included in the laser transmission unit 812 of the laser irradiation unit 801, but also all kinds of factors that can cause attenuation of the laser beam such as the optical connection loss at the optical fiber connector 922, the reflection factor at the laser reflection surface 816, and the laser beam transmission factor of the laser transmissive cover material (not shown) used to cover the window 911 of the urethra insertion unit 811.

Figure 30:
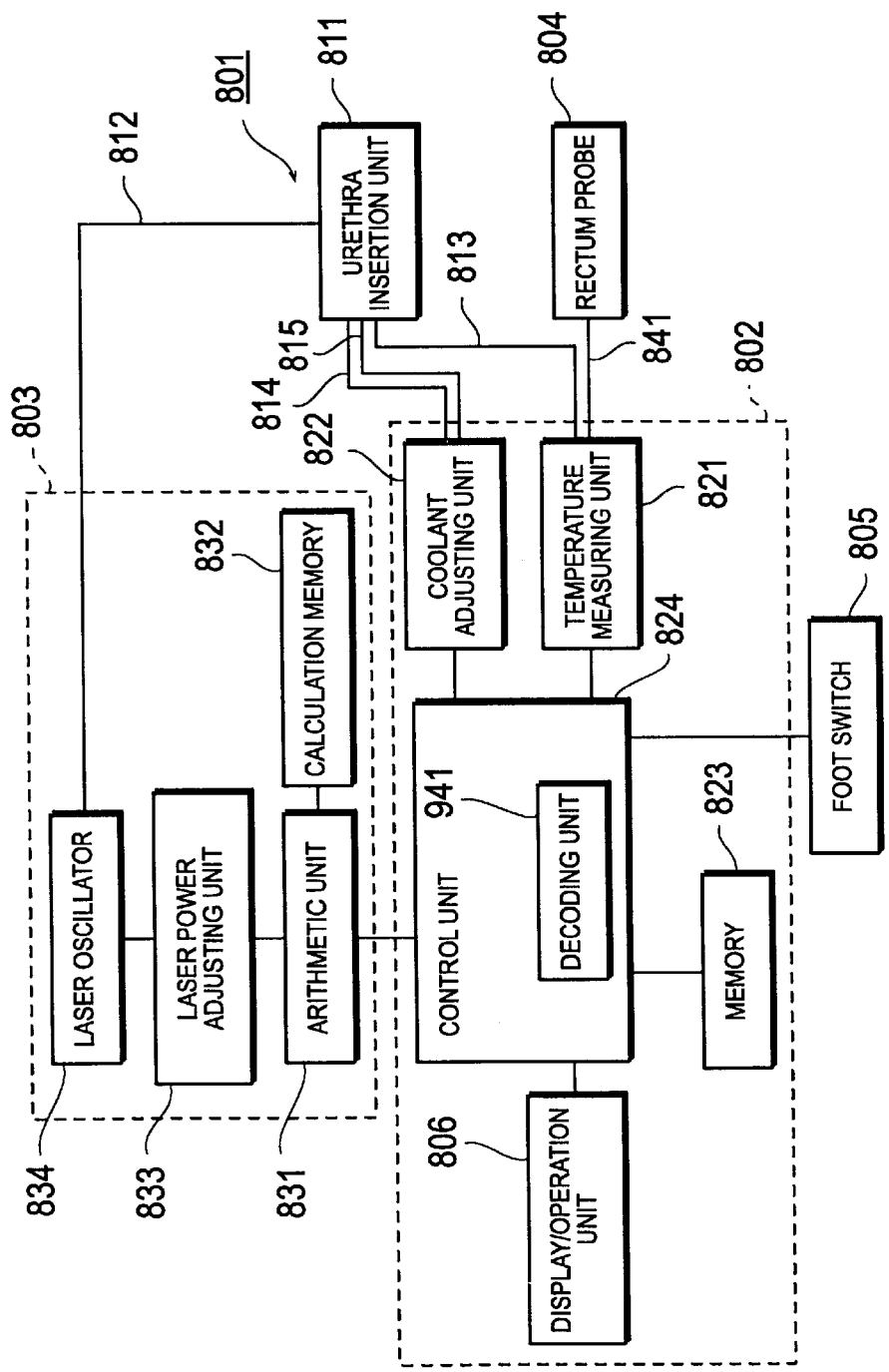
FIG. 30 is a block diagram showing the constitution of the main controller and the laser generator.

Next, the specific constitutions of the main controller 802 and the laser generator 803 will be described referring to FIG. 30. FIG. 30 is a block diagram showing the constitution of the main controller 802 and the laser generator 803.

The main controller 802 is equipped with the display/operation unit 806, a temperature measuring unit 821, a coolant adjusting unit 822, a memory 823, and a control unit 824.

The display/operation unit 806 is a user interface, and enable the user to enter various preset data. The user can preset the laser beam energy value (hereinafter called "irradiation energy value") that is desired to be irradiated by the laser irradiation unit 801 and further enter the abovementioned product identification code assigned to the laser irradiation unit 801 at the display/operation unit 806.

The temperature measuring unit 821 is connected to the laser irradiation unit 801 and the rectum probe 804 that are located outside of the main controller 802, and receive the urethra temperature detected by the laser irradiation unit 801 and the rectum temperature detected by the rectum probe 804. The temperature measuring unit 821 monitors the inputted temperatures and output them to the control unit 824. Therefore, the control unit 824 can control either the laser generator 803 or the coolant adjusting unit 822, or both, based on the temperatures of the tissues monitored by the temperature measuring unit 821, and prevent the normal tissues be heated unnecessarily.

The coolant adjusting unit 822 is connected with the laser irradiating unit 801 via the water supply tube 814 and the drain tube 815. The coolant adjusting unit 822 is controlled by the control unit 824 and adjusts the flow rate and the temperature of the coolant to be supplied to the laser irradiation unit 801. The control unit 824 can be so designed to control the coolant adjusting unit 822 based on the urethra temperature monitored by the temperature measuring unit 821.

The memory 823 stores specified programs and data. The memory 823 stores, for example, a control program for controlling the laser generator 803, and a specified temperature to be used as a reference for judging whether the temperature detected by the laser irradiation unit 801 is abnormally high. The memory 823 accumulates and stores as a history the product identification code entered through the display/operation unit 806.

The control unit 824 controls the laser generator 803 so that the laser beam of the irradiation energy value set up by the user through the display/operation unit 806 be irradiated by the laser irradiation unit 801, and controls the laser generator 803 and the coolant adjusting unit 822 based on the detection results of the temperature sensor 912 provided on the rectum probe 804 and the temperature sensor 913 provided on the rectum insertion unit 811. The control unit 824 is connected to the foot switch 805 and controls the laser generator 803 only when the foot switch is being stepped on by the user. The control unit 824 makes a judgment as to whether the product identification code entered through the display/operation unit 806 is appropriate.

If the product identification code is judged to be appropriate, a decoding unit 941 contained in the control unit 824 decodes the laser beam transmission efficiency of the laser irradiation unit 801 from the product identification code. The control unit 824 makes a judgment as to whether the deciphered laser beam transmission efficiency is appropriate; if it is appropriate, it stores the product identification code as well as the laser beam transmission efficiency information decoded by the decoding unit 941 into the memory 823.

If the product identification code is inappropriate, or if the decoded laser beam transmission efficiency is inappropriate, the control unit 824 displays on the display/operation unit 806 a message that an error occurred, and that the data reentry is required.

The control unit 824 transmits the laser beam transmission efficiency stored in the memory 823 to the laser generator 803 together with the irradiation energy value set up through the display/operation unit 806.

The laser generator 803 is equipped with an arithmetic unit 831, a calculation memory 832, a laser power adjusting unit 833, and a laser oscillator 834.

The arithmetic unit 831 calculates the laser beam energy generation value to be generated by the laser oscillator 834 under the adjustment of the laser power adjusting unit 833 based on the irradiating energy value transmitted from the control unit 824 of the main controller 802 and the laser beam transmission efficiency of the laser irradiation unit 801.

Specifically, the arithmetic unit 831 checks, first of all, how much the laser beam energy actually irradiated from the laser irradiation unit 801 attenuated compared to the laser beam energy amount oscillated by the laser oscillator 834 referencing the laser beam transmission efficiency of the laser irradiation unit 801. Then, it calculates the laser beam energy to be generated by the laser oscillator 834 considering the attenuation by the laser irradiation unit 801 in such away that the laser beam energy actually irradiated by the laser irradiation unit 801 matches with the irradiation energy preset by the user by means of the display/operation unit 806.

For example, if the laser energy preset at the display/operation unit 806 is P (W), and the laser beam transmission efficiency of the laser irradiation unit 801 is T, it calculates P'=P/T, and the laser power adjusting unit 833 causes the laser oscillator 834 to irradiate the laser beam of P' (W) of energy amount.

The arithmetic unit 831 then outputs the laser beam energy to be generated, which is the result of the calculation, to the laser power adjusting unit 833.

The calculation memory 832 stores an arithmetic program to cause the arithmetic unit 831 to perform the abovementioned calculation.

The laser power adjusting unit 833 adjusts the laser power by the laser oscillator 834 based on the laser beam energy amount to be generated, which is issued by the arithmetic unit 831. The laser beam generator 834 is adjusted by the laser power adjusting unit 833 and irradiates laser beams to the laser transmission unit 812.

As can be seen from the above, the thermal treatment apparatus calculates the pre-amplified energy to be generated based on the laser beam attenuation, i.e., the laser beam transmission efficiency, at the laser irradiation unit 801, and causes the laser oscillator 834 accordingly. Therefore, the oscillated energy beam attenuates as it passes through the optical fiber connector 922 of the laser irradiation unit 801, the optical fiber, the laser reflection surface 816, and the cover material, so that the urethra is irradiated with the exact energy preset at the display/operation unit 806.

Next, the process concerning the product identification code by the control unit 824 of the main controller 802 will be described.

Figure 31:
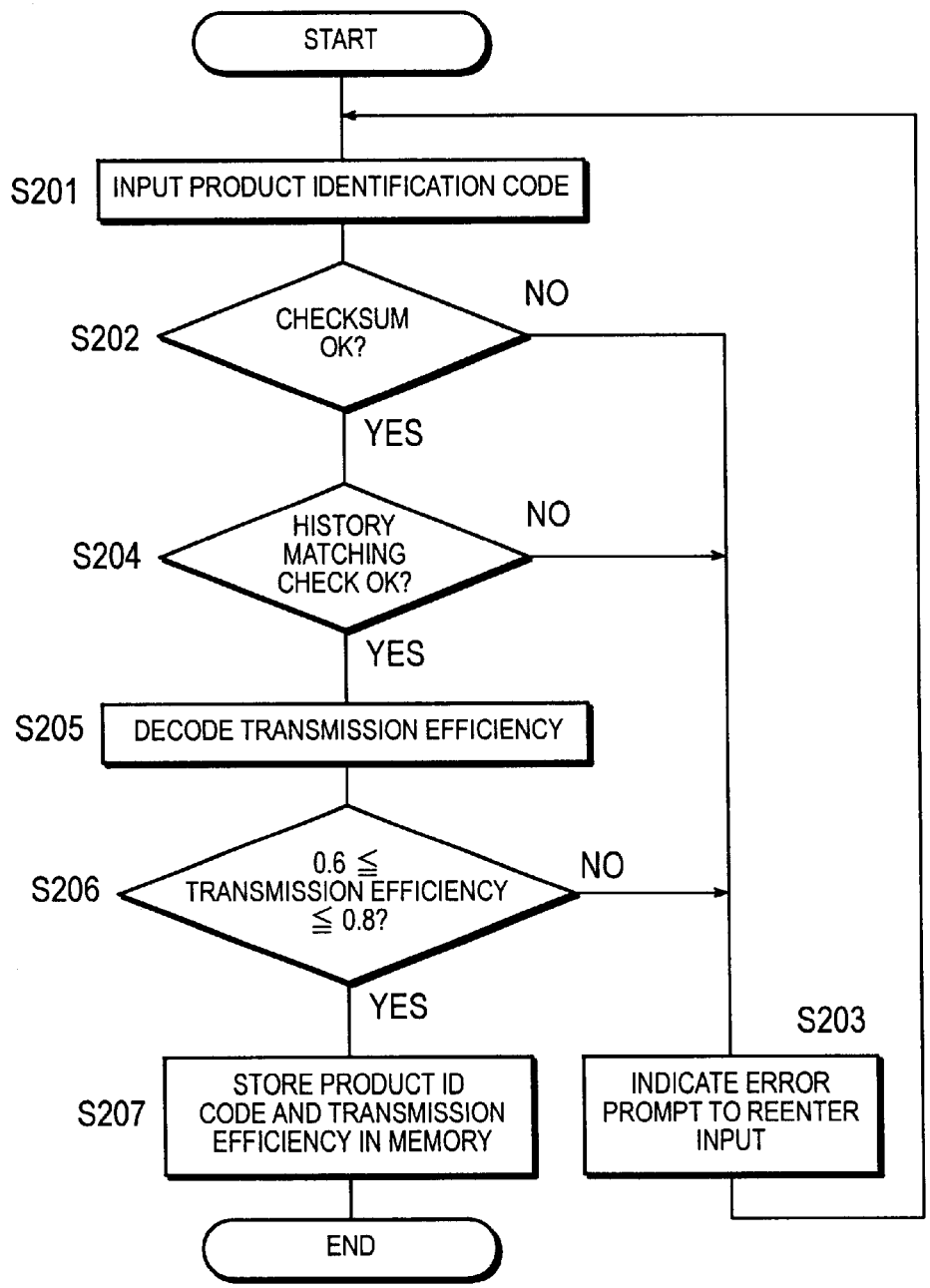
FIG. 31 is a flowchart showing the operation of the control unit of the main controller.

FIG. 31 is a flowchart showing the operation of the control unit 824 of the main controller 802.

In describing the steps of FIG. 31, we assume that the product identification code entered in the display/operation unit 806 is "0123450757."

When a product identification code is entered into the display/operation unit 806, the entered product identification code will be sent to the control unit 824 immediately (S201).

First, the control unit 824 looks at the last digit of the product identification code, "0123450757," i.e., the digit. "7," and determines whether this checksum is a proper one (S202). More specifically, the control unit 824 calculates the sum of all digits in the product identification code except the last (checksum) digit, i.e., "012345075," and determines whether the least significant digit of the sum matches with the checksum digit. If they match (S202: Yes), the system advances to the process of the step S204; if they don't match (S202: No), it means that there is an error in the product identification code so that the system displays on the display/operation unit 806 an error indication and prompts the user to reenter the input data (S203).

In this case, the sum of "012345075" is 27 so that the least significant digit of 27 is "7" and matches with the checksum digit "7." Therefore, the control unit 824 can confirm that there is no input error in the product identification code (S202: Yes).

Next, the control unit 824 checks if the same product identification code as the newly entered product identification code, "0123450757," exists among those that have been entered at the display/operation unit 806 and stored in the memory 823 in the past (S204).

If the same product identification code as the newly entered product identification code, "0123450757," exists among those that have been stored in the memory 823 (S204: Yes), it is assumed that the same product has been used at least once and it is unsanitary to use the same product twice, so that the control unit 824 displays an error indication on the display/operation unit 806 and prompts the user to connect a new laser irradiation unit 801 and enter a new product identification code (S203).

If the product identification code, "0123450757," does not exist among those codes stored in the memory 823 (S204: Yes), the decoding unit 941 decodes (extracts) the laser beam transmission efficiency of the laser irradiation unit 801 from the product identification code (S205). In this case, the decoding unit 941 reads the last fourth to the second digit "075 of the product identification code, and decodes it to mean that the laser transmission efficiency of the laser irradiation unit 801 is 75%.

Next, the control unit 824 makes a judgment as to whether the laser beam transmission efficiency decoded by the decoding unit 941 is higher than 0.6 and lower than 0.8 (S206). If the decoded laser beam transmission efficiency is not higher than 0.6 and not lower than 0.8 (S206: No), the decoded transmission efficiency is an unrealistic value as a product, so that the control unit 824 judges that there is an error in the product identification code, displays an error indication and prompts the user to reenter an input on the display/operation unit 806 (S203).

On the other hand, if the decoded laser beam transmission efficiency is higher than 0.6 and lower than 0.8 (S206: Yes), the control unit 824 judges that there is no error in the product identification code and stores the product identification code and the decoded transfer efficiency in the memory 823 (S207). The product identification code stored here will be used in the history check the next time and thereafter.

As can be seen from the above, the thermal treatment apparatus according to this invention can irradiate tissues always with the laser beam of the irradiation energy value preset for a particular user regardless of individual difference of each laser irradiation unit 801 with a simple input operation, so that a stable treatment effect can be achieved.

Further, the thermal treatment apparatus according to the present invention can prevent the reuse of the laser irradiation unit 801, which is essentially a throwaway product, by not irradiating laser beams if it is found that the same laser irradiation unit 801 was used in the past by checking if there has been any entry of the same product identification number.

Furthermore, since the thermal treatment apparatus according to the present invention is equipped with the arithmetic unit 831 in the laser generator 803, it is possible to adjust the energy amount of the laser beam to be generated even when only the laser generator 803 is to be used.

Although it is described in the above that the product identification code is entered manually at the display/operation unit 806, it is also possible to add a scanner and a character reader in order to read numbers automatically.

Moreover, although the product identification code was expressed in 10 digits, the invention is not limited to it. For example, the product identification code can be such an identification code as a barcode or a two dimensional barcode. In such a case, the display/operation unit 806 can be equipped with an identification code reader such as a barcode reader so that the barcode reader reads the product identification code. A barcode reader prevents input errors, which can be induced by manual inputs.

It is also possible to combine the constitution and control method for adjusting the energy to be generated by the laser generator by obtaining the product identification code as shown in the eighth embodiment (as well as a ninth through tenth embodiments described below-) with the constitutions and control methods for securing preferable reciprocating and stopping motions of the laser emission part as shown in the first through third embodiments.

[Embodiment 9] A ninth embodiment is different from the eighth embodiment in that the arithmetic unit for calculating the laser beam energy to be generated by the laser generator 803 is provided in the main controller 802 rather than in the laser generator 803. Therefore, the basic constitution of the ninth embodiment is almost identical to that of the eighth embodiment, so that constitutional elements identical to those in FIG. 30 are identified by the same reference numbers in order to eliminate the needs for repeating their descriptions. A control unit 825 of the main controller 802 will be described below.

Figure 32:
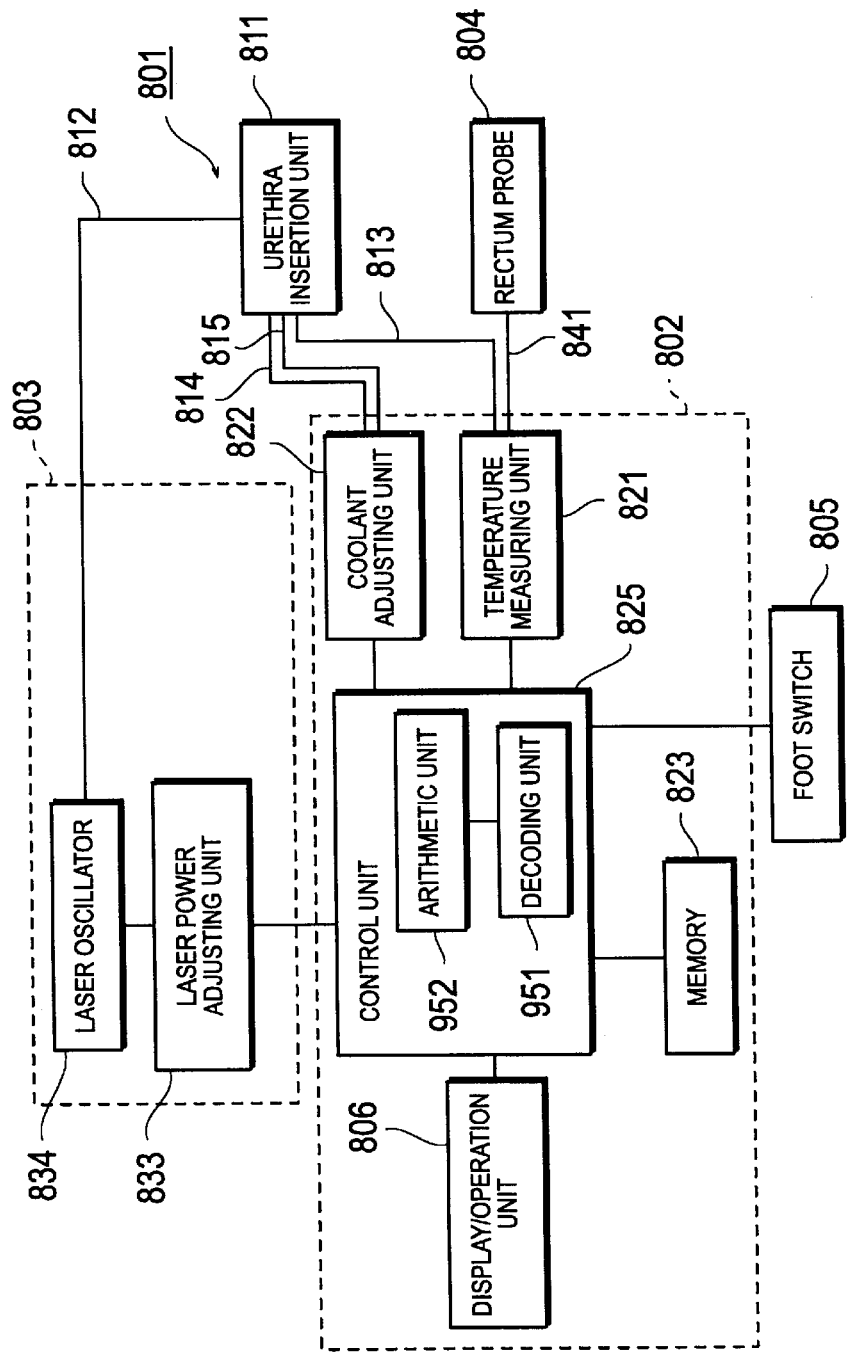
FIG. 32 is a block diagram showing the constitution of the main controller and the laser generator according to a ninth embodiment.

FIG. 32 is a block diagram showing the constitution of the main controller 802 and the laser beam generator 803 according to the ninth embodiment.

The main controller 802 is equipped with the control unit 825. The control unit 825 is equipped with a decoding unit 951 and an arithmetic unit 952.

When the user enters the product identification code of the laser irradiation unit 801 via the display/operation unit 806, the control unit 825 makes a judgment whether the input of the product identification code is correct based on the checksum of the product identification code. If the control unit 825 judges that the input is correct, it collates the inputted product identification code with the history of the product identification stored in the memory 823.

If no matching product identification code can be found in the history, the decoding unit of 951 of the control unit 825 decodes the product identification code and extracts the laser beam transmission efficiency of the laser irradiation unit 801.

The control unit 825 makes a judgment as to whether the extracted laser beam transmission efficiency falls within the specified range, and stores the product identification code and the laser beam transmission efficiency in the memory 823 if it is within the specified range. The arithmetic unit 952 enters the laser beam irradiation energy value preset at the display/operation unit 806 in the arithmetic unit 952 together with the product identification code.

The arithmetic unit 952 calculates the energy value of the laser beam to be generated by the laser generator 803 based on the laser beam transmission efficiency and the irradiation energy value inputted. This calculation is identical that of the eighth embodiment.

The control unit 825 transmits the energy generation value calculated by the arithmetic unit 952 to the laser power adjusting unit 833 of the laser generator 803. As shown in FIG. 32, the main controller 802 and the laser generator 803 are built separately to have separate cabinets of their own. Moreover, since the arithmetic unit 952 is provided in the control unit 825 of the main controller 802, the laser generator 803 can be used as a general purpose unit rather than a dedicated unit. Therefore, it is possible to combine different laser generators with the main controller 802 arbitrarily as long as the signal specification is within the same range.

For example, it is possible to have multiple laser generators with different rated laser beam power values and to make different combinations as needed. Thus, the system use of the thermal treatment apparatus can be improved and various laser generators 803 can be easily replaced, improving their maintenance capability.

[Embodiment 10] In the eighth and ninth embodiments, the product identification code is entered via the display/operation unit 806 and the laser beam transmission efficiency of the laser irradiation unit 801 is extracted from the product identification code. However, in a tenth embodiment, a resistor is provided in a laser irradiation unit 860 and the laser beam transmission efficiency is extracted from the resistance value of this resistor.

Since the basic constitution of the tenth embodiment is almost identical to that of the eighth and the ninth embodiments, their constitutional elements are identified by assigning identical reference numbers as in FIG. 30 and their descriptions are not repeated here.

The laser irradiation 860 will be described below.

Figure 33:
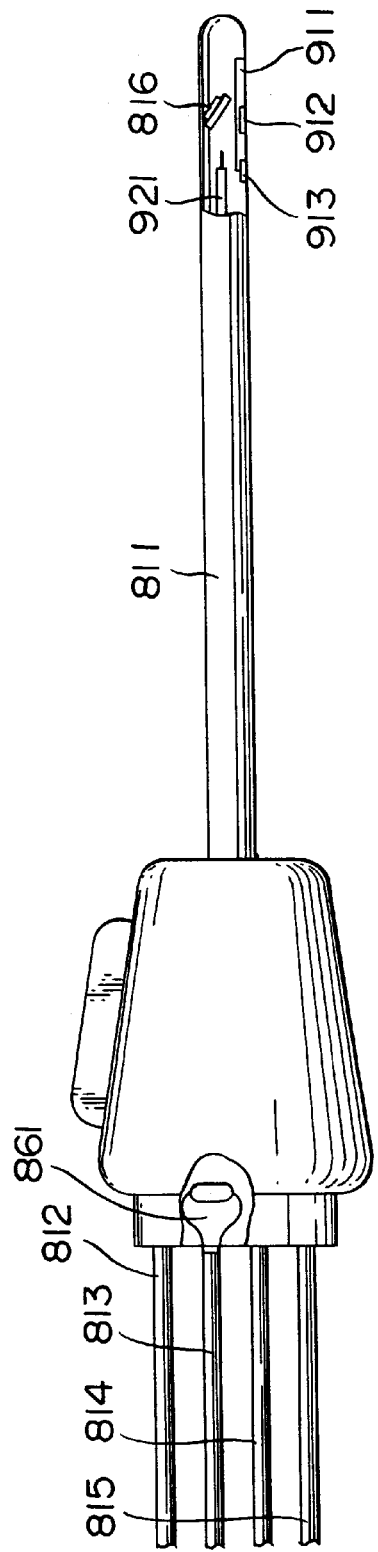
FIG. 33 is an enlarged diagram of a laser irradiation unit according to a tenth embodiment.

FIG. 33 is an enlarged view of the laser beam irradiation unit 860 in the tenth embodiment.

The laser irradiation unit 860 in the tenth embodiment has a resistor 861 inside. The resistor 861 has a resistance comparable to the laser beam transmission efficiency of the laser irradiation unit 860 measured in the manufacturing stage. For example, if the laser beam transmission efficiency of the laser irradiation unit 860 is 80%, the resistance of the resistor 861 to be built into this laser irradiation unit 860 should be determined to be 80 kΩ.

The resistor 861 is connected to the main controller 802 via lead wires that go through the urethra signal cable 813.

The main controller 802 detects the resistance value of the resistor 861 via the lead wires and measures the laser beam transmission efficiency of the laser irradiation unit 860 connected to the laser generator 803.

As can be seen from the above, the tenth embodiment can save the effort of manually inputting the product identification code through the display/operation unit 806 and prevent input errors.

Although it was described in the eighth through tenth embodiments that the laser irradiation units 801 and 860 includes the urethra insertion unit 811 to be used in the benign prostatic hyperplasia, the invention is not limited by it. The laser irradiation unit 801 or 860 can be various other treatment instruments to be inserted into body cavities and blood vessels for irradiating energy to body cavities and blood vessels. Moreover, it is possible to constitute the laser irradiation unit 801 or 860 to have an endoscope as an observation member built in for observing the target area.

Although the laser irradiation unit 801 or 860 is described as a single use item in the eighth through the tenth embodiments, the invention is not limited to it. Since the urethra insertion unit 811 is the only item of the laser irradiation unit 801 or 860 that is actually inserted into the human body, it can be so constituted to replace only its housing. If only the housing is to be replaced, it is possible to prevent the reuse of the housing by detecting the reuse of the housing as described above by inputting the product identification code assigned to the housing into the main controller 802. By replacing only the housing, cost reduction can be achieved without sacrificing the sanitary level.

It is obvious that this invention is not limited to the particular embodiments shown and described above but may be variously changed and modified without departing from the technical concept of this invention.

Although laser beam is assumed as the energy to be irradiated toward tissues in the above descriptions, the invention is not limited to it. The energy can be microwave, radio frequency, ultrasound, etc.

Although prostate was assumed as the living tissue to be thermally treated, the invention is not limited to it, but rather the applicable tissues include all other tissues such as blood vessels, digestive tubes (gullet, bowel, etc.), and abdominal cavity that can be thermally treated by irradiating energy internally or from the outside of the body.

This application is based on Japanese Patent Application No. 2001-198786 filed on Jun. 29, 2001, the contents of which are hereby incorporated by reference.

What is claimed is:

1. A thermal treatment apparatus comprising:
   an energy supply unit for supplying energy for treatment;
   an energy irradiation unit for applying energy supplied by said energy supply unit to a vital tissue, said energy irradiation unit having a movable energy emission part for emitting energy toward the tissue, a driving device for causing said energy emission part to reciprocate, and a guide lumen adapted to supports an observation member for observing the tissue in such a way as to be able to move in the direction of the movement of said energy emission part; and
   a control unit for controlling said energy emission part to stop at a position where the energy emission part does not interfere with the moving passage of said observation member when stopping the motion of said driving device.

2. A thermal treatment apparatus as claimed in claim 1, wherein
   said energy irradiation unit further has a position detection device for detecting the position of said energy emission part, and
   said control unit controls said energy emission part to stop based on a signal from said position detection device.

3. A thermal treatment apparatus as claimed in claim 1, wherein
   said energy irradiation unit further has a long and slender main body that can be inserted into a living body, and an interlocking means that changes the energy emission angle for emitting the energy toward the tissue in accordance with the movement of said energy emission part.

4. A thermal treatment apparatus as claimed in claim 1, wherein
   said energy is a laser beam.

5. A thermal treatment apparatus as claimed in claim 1 further comprising:
   an irradiation instruction unit for instructing the start of energy irradiation, and
   an irradiation time period setup unit for setting energy irradiation time period, wherein
      said control unit has an irradiation control unit for controlling said energy supply unit to deliver the energy for a preset irradiation time period, which is setup by said irradiation time period setup unit, based on an energy irradiation start instruction received from said irradiation instruction unit, and
      said irradiation control unit sets up a new irradiation time period when another energy irradiation start instruction is received from said irradiation instruction unit after energy irradiation for said preset irradiation time period is completed.

6. A thermal treatment apparatus as claimed in claim 5, wherein
   an upper limit for the number of cycles where the irradiation time period can be set through said irradiation time period setting unit is predetermined.

7. A thermal treatment apparatus as claimed in claim 5, further comprising:
   an extension instruction unit for instructing an extension of energy irradiation time period, wherein
      if an instruction for irradiation time period extension is indicated during an irradiation of energy, a new irradiation time period is added to the irradiation time period preset for the energy currently being irradiated.

8. A thermal treatment apparatus as claimed in claim 7, wherein
   said new irradiation time period is determined as a function of the initially set irradiation time period.

9. A thermal treatment apparatus as claimed in claim 5, further comprising:
   a notification means for notifying that an instruction for starting irradiation has been issued when said irradiation instruction unit has issued the instruction, wherein
      said irradiation control unit controls said energy supply unit when an irradiation start instruction has been on for a certain period of time by said irradiation instruction unit.

10. A thermal treatment apparatus as claimed in claim 5, wherein
    said energy is a laser beam.

11. A thermal treatment apparatus as claimed in claim 1, further comprising:
    a temperature measuring device for measuring the vital tissue's temperature;
    an irradiation instruction unit for instructing the start of energy irradiation, and
    an irradiation time period setup unit for setting energy irradiation time period, wherein
       said control unit has an irradiation control unit for controlling said energy supply unit to deliver the energy for a preset irradiation time period, which is setup by said irradiation time period setup unit, based on an energy irradiation start instruction received from said irradiation instruction unit, and
       said irradiation control unit sets up a new irradiation time period when restarting of energy irradiation is instructed by said irradiation instruction unit after said predetermined time period of energy irradiation has been completed, monitors the tissue's temperature measured by said temperature measuring device during the energy irradiation of said new irradiation time period, and stops irradiating energy when the tissue's temperature becomes higher than a specified temperature.

12. A thermal treatment apparatus as claimed in claim 1, further comprising:
    an acquisition unit for acquiring a product identification code assigned to said energy irradiation unit;
    a setup unit for setting up irradiation value of energy to be emitted from said energy irradiation unit;

an arithmetic unit for calculating generation value of energy to be generated by said supply unit based on said product identification code and said irradiation value of energy; and an adjusting unit for adjusting energy generating amount of said energy supply unit based on said generation value of energy.

13. A thermal treatment apparatus as claimed in claim 12, further comprising:

a memory unit for storing the product identification code acquired by said acquisition unit; and a searching unit that, when a new product identification code is acquired from said acquisition unit, searches said new product identification code among product identification codes stored in said memory unit, wherein the energy supply unit does not supply the energy when said new product identification code is found among product identification codes stored in said memory unit as a result of searching by said searching unit.

14. A thermal treatment apparatus as claimed in claim 12, wherein said product identification code includes the information concerning said energy irradiation unit's energy transmission efficiency.

15. A thermal treatment apparatus as claimed in claim 12, wherein said acquisition unit acquires said product identification code received via a user interface.

16. A thermal treatment apparatus as claimed in claim 12, wherein said product identification code is expressed in terms of an identification symbol; and said acquisition unit acquires said product identification code by reading said identification symbol.

17. A thermal treatment apparatus as claimed in claim 12, wherein said product identification code is expressed in terms of resistance value of a resistor attached to said energy irradiation unit, and said acquisition unit acquires said product identification code by measuring said resistor's resistance value.

18. A thermal treatment apparatus as claimed in claim 12, wherein said energy is a laser beam.

19. A thermal treatment apparatus as claimed in claim 12, wherein said energy irradiation unit includes a treatment instrument for benign prostatic hyperplasia.

20. A thermal treatment apparatus as claimed in claim 18, wherein said energy irradiation unit further has an observation member for observing the tissue.

21. A thermal treatment apparatus comprising:

an energy supply unit for supplying energy for treatment;

an energy irradiation unit for applying energy supplied by said energy supply unit to a vital tissue, said energy irradiation unit having a movable energy emission part for emitting energy toward the tissue, a driving device for causing said energy emission part to reciprocate, a guide lumen that supports an observation member for observing the tissue in such a way as to be able to move in the direction of the movement of said energy emission part, and a motion detection device for detecting the movement of said observing member to a specified position; and a control unit for controlling said energy emission part to stop when the movement of said observing member to said specified position is detected.

22. A thermal treatment apparatus as claimed in claim 21, wherein said control unit controls said energy emission part to stop at a position where the energy emission part does not interfere with the moving passage of said observing member when the movement of said observing member to said specified position is detected.

23. A thermal treatment apparatus as claimed in claim 22, wherein said energy irradiation unit further has a position detection device for detecting the position of said energy emission part, and said control unit controls said energy emission part to stop based on a signal from said position detection device.

24. A thermal treatment apparatus as claimed in claim 21, wherein said control unit further controls said energy supplying unit to stop supplying energy when the movement of said observing member to said specified position is detected.

25. A thermal treatment apparatus comprising:

an energy supply unit for supplying energy for treatment;

an energy irradiation unit for applying energy supplied by said energy supply unit to a vital tissue, said energy irradiation unit having a movable energy emission part for emitting energy toward the tissue, a driving device for causing said energy emission part to reciprocate, and a reciprocating motion detection device for detecting the reciprocating motion of said energy emission part;

an irradiation operating unit for instructing said energy supply unit to start or stop the supply of energy; and a control unit for controlling said energy emission part to conduct reciprocating motion and for causing said energy supply unit to start supplying energy if the result of detection by said reciprocating motion detection device meets a specified tolerance condition within a specified time period when an energy supply start instruction is received from said irradiation operating unit.

26. A thermal treatment apparatus as claimed in claim 25 further comprising:

a notification means for notifying the operator that it is within said specified time.

* * * * *